US012508024B2

(12) United States Patent
Jasemian et al.

(10) Patent No.: US 12,508,024 B2
(45) Date of Patent: *Dec. 30, 2025

(54) SURGICAL STAPLING INSTRUMENTS

(71) Applicant: INTUITIVE SURGICAL OPERATIONS, INC., Sunnyvale, CA (US)

(72) Inventors: Babak Jasemian, Trabuco Canyon, CA (US); Tibor Laszlo Hites, Sonora, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/271,384

(22) PCT Filed: Dec. 29, 2021

(86) PCT No.: PCT/US2021/065544

§ 371 (c)(1),
(2) Date: Jul. 7, 2023

(87) PCT Pub. No.: WO2022/150215

PCT Pub. Date: Jul. 14, 2022

(65) Prior Publication Data

US 2024/0065690 A1 Feb. 29, 2024

Related U.S. Application Data

(60) Provisional application No. 63/134,962, filed on Jan. 8, 2021.

(51) Int. Cl.
*A61B 17/29* (2006.01)
*A61B 17/072* (2006.01)
(Continued)

(52) U.S. Cl.
CPC ........ *A61B 17/07207* (2013.01); *A61B 34/37* (2016.02); *A61B 90/98* (2016.02);
(Continued)

(58) Field of Classification Search
CPC ... A61B 17/07207; A61B 34/37; A61B 90/98; A61B 2017/0003; A61B 2017/07271;
(Continued)

(56) References Cited

U.S. PATENT DOCUMENTS 75,364 A 3/1868 Case
3,792,597 A 2/1974 Orain et al.
(Continued)

FOREIGN PATENT DOCUMENTS

AU 2014259544 A1 * 9/2015 ........... A61B 17/068
CN 103889344 A 6/2014
(Continued)

OTHER PUBLICATIONS

Field Application Note—Journal Bearings, Retrieved from Wayback Machine URL: https://web.archive.org/web/20100110095051/ http://www.reliabilitydirect.com/appnotes/jb.html, on Mar. 12, 2024, 04 pages.

(Continued)

*Primary Examiner* — Robert F Long
(74) *Attorney, Agent, or Firm* — Farber LLC

(57) ABSTRACT

Surgical stapling instruments include mechanisms for identifying and/or deactivating stapler cartridges for use with the instruments. The stapling instrument includes a drive member for actuating a staple cartridge and a locking member movable from a disabled position permitting distal translation of the drive member through a staple firing stroke, to a locking position inhibiting distal translation of the drive member through the staple firing stroke. The staple cartridge may include a switch movable in a lateral direction to either (Continued)

maintain the locking member in the disabled position or to allow the locking member to move into the locking position.

20 Claims, 29 Drawing Sheets

(51) Int. Cl.
*A61B 34/37* (2016.01)
*A61B 90/98* (2016.01)
*A61B 17/00* (2006.01)
*A61B 34/30* (2016.01)

(52) U.S. Cl.
CPC ................. *A61B 2017/0003* (2013.01); *A61B 2017/07271* (2013.01); *A61B 2017/2946* (2013.01); *A61B 2034/302* (2016.02)

(58) Field of Classification Search
CPC ...... A61B 2017/2946; A61B 2034/302; A61B 34/30; A61B 90/90; A61B 2017/00017; A61B 2017/00314; A61B 2017/07278; A61B 2017/07285; A61B 2090/066; A61B 2090/0814
USPC ................................ 227/175.1–182.1, 8, 19
See application file for complete search history.

(56) References Cited

U.S. PATENT DOCUMENTS 4,305,539 A 12/1981 Korolkov et al.
4,319,576 A 3/1982 Rothfuss
4,352,276 A 10/1982 Smith
4,403,892 A 9/1983 Kane
4,407,286 A 10/1983 Noiles et al.
4,429,695 A 2/1984 Green
4,509,518 A 4/1985 McGarry et al.
4,509,932 A 4/1985 Weible
4,605,001 A 8/1986 Rothfuss et al.
4,608,981 A 9/1986 Rothfuss et al.
4,610,383 A 9/1986 Rothfuss et al.
4,633,874 A 1/1987 Chow et al.
4,767,044 A 8/1988 Green
4,809,695 A 3/1989 Gwathmey
4,848,637 A 7/1989 Pruitt
4,892,244 A 1/1990 Fox et al.
4,930,503 A 6/1990 Pruitt
4,978,049 A 12/1990 Green
5,007,300 A 4/1991 Siva
5,027,834 A 7/1991 Pruitt
5,040,715 A 8/1991 Green et al.
5,133,735 A 7/1992 Slater et al.
5,133,736 A 7/1992 Bales, Jr. et al.
5,142,931 A 9/1992 Menahem
5,147,357 A 9/1992 Rose et al.
5,180,092 A 1/1993 Crainich
5,242,457 A 9/1993 Akopov et al.
5,275,323 A 1/1994 Schulze et al.
5,307,976 A 5/1994 Olson et al.
5,312,023 A 5/1994 Green et al.
5,316,435 A 5/1994 Mozingo
5,334,183 A 8/1994 Wuchinich
5,342,395 A 8/1994 Jarrett et al.
5,342,396 A 8/1994 Cook
5,366,133 A 11/1994 Geiste
5,452,836 A 9/1995 Huitema et al.
5,452,837 A 9/1995 Williamson, IV et al.
5,465,895 A * 11/1995 Knodel ............ A61B 17/07207 227/176.1
5,480,089 A 1/1996 Blewett
5,484,095 A 1/1996 Green et al.
5,484,451 A 1/1996 Akopov et al.
5,487,500 A 1/1996 Knodel et al.
5,497,931 A 3/1996 Nakamura
5,533,521 A 7/1996 Granger
5,540,375 A 7/1996 Bolanos et al.
5,554,164 A 9/1996 Wilson et al.
5,560,530 A 10/1996 Bolanos et al.
5,562,239 A 10/1996 Boiarski et al.
5,564,615 A 10/1996 Bishop et al.
5,571,116 A 11/1996 Bolanos et al.
5,571,285 A 11/1996 Chow et al.
5,573,534 A 11/1996 Stone
5,573,543 A 11/1996 Akopov et al.
5,607,449 A 3/1997 Tontarra
5,615,820 A 4/1997 Viola
5,624,452 A 4/1997 Yates
5,628,446 A 5/1997 Geiste et al.
5,632,432 A 5/1997 Schulze et al.
5,651,491 A 7/1997 Heaton et al.
5,652,849 A 7/1997 Conway et al.
5,667,626 A 9/1997 Cayford et al.
5,673,840 A 10/1997 Schulze et al.
5,673,842 A 10/1997 Bittner et al.
5,676,674 A 10/1997 Bolanos et al.
5,688,269 A 11/1997 Newton et al.
5,690,269 A 11/1997 Bolanos et al.
5,693,042 A 12/1997 Boiarski et al.
5,697,542 A 12/1997 Knodel et al.
5,700,270 A 12/1997 Peyser et al.
5,700,276 A 12/1997 Benecke
5,704,534 A 1/1998 Huitema et al.
5,709,680 A 1/1998 Yates et al.
5,738,474 A 4/1998 Blewett
5,752,644 A 5/1998 Bolanos et al.
5,752,973 A 5/1998 Kieturakis et al.
5,762,255 A 6/1998 Chrisman et al.
5,762,256 A 6/1998 Mastri et al.
5,779,130 A 7/1998 Alesi et al.
5,782,396 A 7/1998 Mastri et al.
5,792,135 A 8/1998 Madhani et al.
5,820,009 A 10/1998 Melling et al.
5,826,776 A 10/1998 Schulze et al.
5,833,695 A 11/1998 Yoon
5,865,361 A 2/1999 Milliman et al.
5,871,135 A 2/1999 Williamson, IV et al.
5,911,353 A 6/1999 Bolanos et al.
5,915,616 A 6/1999 Viola et al.
5,919,198 A 7/1999 Graves, Jr. et al.
5,941,442 A 8/1999 Geiste et al.
5,954,259 A 9/1999 Viola et al.
5,959,892 A 9/1999 Lin et al.
6,032,849 A 3/2000 Mastri et al.
6,050,996 A 4/2000 Schmaltz et al.
6,079,606 A 6/2000 Milliman et al.
6,113,598 A 9/2000 Baker
6,126,666 A 10/2000 Trapp et al.
6,174,309 B1 1/2001 Wrublewski et al.
6,202,914 B1 3/2001 Geiste et al.
6,241,139 B1 6/2001 Milliman et al.
6,250,532 B1 6/2001 Green et al.
6,312,426 B1 11/2001 Goldberg et al.
6,330,956 B1 12/2001 Willinger
6,330,985 B1 12/2001 Milliman et al.
6,443,973 B1 * 9/2002 Whitman ......... A61B 17/07207 227/176.1
6,488,196 B1 12/2002 Fenton, Jr.
6,503,259 B2 1/2003 Huxel et al.
6,582,451 B1 6/2003 Marucci et al.
6,585,735 B1 7/2003 Frazier et al.
6,644,532 B2 11/2003 Green et al.
6,656,193 B2 12/2003 Grant et al.
6,669,073 B2 12/2003 Milliman et al.
6,692,363 B1 2/2004 Heutschi et al.
6,770,072 B1 8/2004 Truckai et al.
6,786,382 B1 9/2004 Hoffman
6,793,652 B1 * 9/2004 Whitman ............... A61B 17/00 606/1
6,817,974 B2 11/2004 Cooper et al.
6,840,938 B1 1/2005 Morley et al.
6,877,647 B2 4/2005 Green et al.
6,905,057 B2 6/2005 Swayze et al.
6,953,139 B2 10/2005 Milliman et al.

(56) References Cited

U.S. PATENT DOCUMENTS

| | | | | |
|---|---|---|---|---|
| 6,955,608 | B1 | 10/2005 | Lutz | |
| 6,959,852 | B2 | 11/2005 | Shelton, IV et al. | |
| 6,964,363 | B2 | 11/2005 | Wales et al. | |
| 6,978,921 | B2 | 12/2005 | Shelton, IV et al. | |
| 6,978,922 | B2 | 12/2005 | Bilotti et al. | |
| 6,981,941 | B2 * | 1/2006 | Whitman | A61B 34/71 606/1 |
| 6,985,133 | B1 | 1/2006 | Rodomista et al. | |
| 6,986,451 | B1 | 1/2006 | Mastri et al. | |
| 6,988,649 | B2 | 1/2006 | Shelton, IV et al. | |
| 7,000,818 | B2 | 2/2006 | Shelton, IV et al. | |
| 7,000,819 | B2 | 2/2006 | Swayze et al. | |
| 7,044,352 | B2 | 5/2006 | Shelton, IV et al. | |
| 7,044,353 | B2 | 5/2006 | Mastri et al. | |
| 7,055,730 | B2 | 6/2006 | Ehrenfels et al. | |
| 7,055,731 | B2 | 6/2006 | Shelton, IV et al. | |
| 7,059,508 | B2 | 6/2006 | Shelton, IV et al. | |
| 7,070,083 | B2 | 7/2006 | Jankowski | |
| 7,114,642 | B2 | 10/2006 | Whitman | |
| 7,128,253 | B2 | 10/2006 | Mastri et al. | |
| 7,140,527 | B2 | 11/2006 | Ehrenfels et al. | |
| 7,140,528 | B2 | 11/2006 | Shelton, IV et al. | |
| 7,258,262 | B2 | 8/2007 | Mastri et al. | |
| 7,296,722 | B2 | 11/2007 | Ivanko | |
| 7,308,998 | B2 | 12/2007 | Mastri et al. | |
| 7,328,828 | B2 | 2/2008 | Ortiz et al. | |
| 7,380,695 | B2 | 6/2008 | Doll et al. | |
| 7,380,696 | B2 | 6/2008 | Shelton, IV et al. | |
| 7,398,908 | B2 | 7/2008 | Holsten et al. | |
| 7,401,721 | B2 | 7/2008 | Holsten et al. | |
| 7,407,075 | B2 | 8/2008 | Holsten et al. | |
| 7,455,676 | B2 | 11/2008 | Holsten et al. | |
| 7,472,814 | B2 | 1/2009 | Mastri et al. | |
| 7,481,349 | B2 | 1/2009 | Holsten et al. | |
| 7,491,202 | B2 | 2/2009 | Odom et al. | |
| 7,494,039 | B2 | 2/2009 | Racenet et al. | |
| 7,561,141 | B2 | 7/2009 | Shahoian et al. | |
| 7,565,993 | B2 | 7/2009 | Milliman et al. | |
| 7,588,174 | B2 | 9/2009 | Holsten et al. | |
| 7,654,431 | B2 | 2/2010 | Hueil et al. | |
| 7,658,312 | B2 | 2/2010 | Vidal et al. | |
| 7,673,783 | B2 | 3/2010 | Morgan et al. | |
| 7,699,835 | B2 | 4/2010 | Lee et al. | |
| 7,721,930 | B2 | 5/2010 | McKenna et al. | |
| 7,726,539 | B2 | 6/2010 | Holsten et al. | |
| 7,770,774 | B2 | 8/2010 | Mastri et al. | |
| 7,780,577 | B2 | 8/2010 | Arnold | |
| 7,794,475 | B2 | 9/2010 | Hess et al. | |
| 7,832,611 | B2 | 11/2010 | Boyden et al. | |
| 7,837,079 | B2 | 11/2010 | Holsten et al. | |
| 7,866,526 | B2 | 1/2011 | Green et al. | |
| 7,942,303 | B2 | 5/2011 | Shah et al. | |
| 7,950,561 | B2 | 5/2011 | Aranyi | |
| 8,070,035 | B2 | 12/2011 | Holsten et al. | |
| 8,083,118 | B2 | 12/2011 | Milliman et al. | |
| 8,127,975 | B2 | 3/2012 | Olson et al. | |
| 8,157,152 | B2 | 4/2012 | Holsten et al. | |
| 8,272,553 | B2 | 9/2012 | Mastri et al. | |
| 8,308,042 | B2 | 11/2012 | Aranyi | |
| 8,348,127 | B2 | 1/2013 | Marczyk | |
| 8,365,972 | B2 | 2/2013 | Aranyi et al. | |
| 8,371,492 | B2 | 2/2013 | Aranyi et al. | |
| 8,439,246 | B1 | 5/2013 | Knodel | |
| 8,490,851 | B2 | 7/2013 | Blier et al. | |
| 8,551,091 | B2 | 10/2013 | Couture et al. | |
| 8,573,465 | B2 | 11/2013 | Shelton, IV | |
| 8,579,178 | B2 | 11/2013 | Holsten et al. | |
| 8,608,047 | B2 | 12/2013 | Holsten et al. | |
| 8,672,206 | B2 | 3/2014 | Aranyi et al. | |
| 8,672,939 | B2 | 3/2014 | Garrison | |
| 8,685,016 | B2 * | 4/2014 | Wham | A61B 18/1442 606/51 |
| 8,701,960 | B1 | 4/2014 | Manoux et al. | |
| 8,783,541 | B2 | 7/2014 | Shelton, IV et al. | |
| 8,800,841 | B2 | 8/2014 | Ellerhorst et al. | |
| 8,834,518 | B2 | 9/2014 | Faller et al. | |
| 8,851,355 | B2 | 10/2014 | Aranyi et al. | |
| 8,852,174 | B2 | 10/2014 | Burbank | |
| 8,858,547 | B2 | 10/2014 | Brogna | |
| 8,864,010 | B2 | 10/2014 | Williams | |
| 8,876,857 | B2 | 11/2014 | Burbank | |
| 8,905,287 | B2 | 12/2014 | Racenet et al. | |
| 8,925,785 | B2 | 1/2015 | Holsten et al. | |
| 9,010,606 | B2 | 4/2015 | Aranyi et al. | |
| 9,016,545 | B2 | 4/2015 | Aranyi et al. | |
| 9,055,961 | B2 | 6/2015 | Manzo et al. | |
| 9,161,807 | B2 | 10/2015 | Garrison | |
| 9,192,378 | B2 | 11/2015 | Aranyi et al. | |
| 9,192,379 | B2 | 11/2015 | Aranyi et al. | |
| 9,211,120 | B2 | 12/2015 | Scheib et al. | |
| 9,216,019 | B2 | 12/2015 | Schmid et al. | |
| 9,307,986 | B2 | 4/2016 | Hall et al. | |
| 9,316,267 | B2 | 4/2016 | Lenz et al. | |
| 9,345,479 | B2 | 5/2016 | Racenet et al. | |
| 9,498,215 | B2 | 11/2016 | Duque et al. | |
| 9,681,870 | B2 | 6/2017 | Baxter, III et al. | |
| 9,717,497 | B2 | 8/2017 | Zerkle et al. | |
| 9,717,498 | B2 | 8/2017 | Aranyi et al. | |
| 9,757,126 | B2 | 9/2017 | Cappola | |
| 9,777,459 | B2 | 10/2017 | Zuritis | |
| 9,808,246 | B2 * | 11/2017 | Shelton, IV | A61B 17/07207 |
| 9,877,721 | B2 * | 1/2018 | Schellin | A61B 17/068 |
| 9,936,949 | B2 | 4/2018 | Measamer et al. | |
| 10,111,659 | B2 | 10/2018 | Racenet et al. | |
| 10,130,367 | B2 | 11/2018 | Cappola et al. | |
| 10,231,732 | B1 | 3/2019 | Racenet et al. | |
| 10,231,733 | B2 | 3/2019 | Ehrenfels et al. | |
| 10,285,693 | B2 | 5/2019 | Kimsey et al. | |
| 10,335,147 | B2 * | 7/2019 | Rector | A61B 17/068 |
| 10,363,037 | B2 | 7/2019 | Aronhalt et al. | |
| 10,383,628 | B2 | 8/2019 | Kang et al. | |
| 10,646,219 | B2 | 5/2020 | Racenet et al. | |
| 10,722,233 | B2 | 7/2020 | Wellman | |
| 10,828,027 | B2 | 11/2020 | Racenet et al. | |
| 10,863,988 | B2 | 12/2020 | Patel et al. | |
| 10,912,556 | B2 | 2/2021 | Burbank | |
| 10,973,517 | B2 | 4/2021 | Wixey | |
| 11,014,224 | B2 | 5/2021 | Dey, IV et al. | |
| 11,020,138 | B2 | 6/2021 | Ragosta | |
| 11,166,773 | B2 | 11/2021 | Ragosta et al. | |
| 11,185,331 | B2 * | 11/2021 | Adams | A61B 17/07207 |
| 11,191,542 | B2 | 12/2021 | Miller et al. | |
| 11,234,700 | B2 | 2/2022 | Ragosta et al. | |
| 11,266,409 | B2 | 3/2022 | Huitema et al. | |
| 11,291,445 | B2 * | 4/2022 | Shelton, IV | A61B 90/90 |
| 11,439,390 | B2 | 9/2022 | Patel et al. | |
| 11,504,124 | B2 | 11/2022 | Patel et al. | |
| 11,517,312 | B2 * | 12/2022 | Wixey | A61B 17/2841 |
| 11,607,219 | B2 | 3/2023 | Shelton, IV et al. | |
| 11,642,129 | B2 | 5/2023 | Burbank | |
| 11,696,758 | B2 * | 7/2023 | Murphy | A61B 17/072 227/180.1 |
| 11,723,661 | B2 | 8/2023 | Wixey et al. | |
| 11,759,202 | B2 * | 9/2023 | Morgan | A61B 17/072 227/175.1 |
| 11,786,325 | B2 | 10/2023 | Mustufa et al. | |
| 11,806,015 | B2 | 11/2023 | Wixey et al. | |
| 11,857,188 | B2 | 1/2024 | Hites | |
| 11,864,762 | B2 | 1/2024 | Wixey | |
| 11,896,224 | B2 | 2/2024 | Wellman | |
| 11,903,583 | B2 | 2/2024 | Burbank et al. | |
| 11,944,301 | B2 | 4/2024 | Wixey et al. | |
| 11,944,302 | B2 | 4/2024 | Wixey et al. | |
| 11,986,184 | B2 | 5/2024 | Patel et al. | |
| 12,000,280 | B2 | 6/2024 | King | |
| 12,011,168 | B2 | 6/2024 | Wixey | |
| 12,029,426 | B2 | 7/2024 | Millman et al. | |
| 12,029,473 | B2 | 7/2024 | Whitlock et al. | |
| 12,089,844 | B2 | 9/2024 | Patel et al. | |
| 12,137,903 | B2 | 11/2024 | Patel et al. | |
| 12,156,654 | B2 | 12/2024 | Wellman | |
| 12,251,107 | B2 | 3/2025 | Wixey et al. | |
| 12,262,891 | B2 | 4/2025 | Burbank | |
| 12,303,130 | B2 | 5/2025 | Wixey et al. | |

(56) References Cited

U.S. PATENT DOCUMENTS 12,324,589 B2 6/2025 Kerver et al.
12,349,905 B2 7/2025 Wellman
2002/0165562 A1 11/2002 Grant et al.
2002/0177843 A1 11/2002 Anderson et al.
2002/0188293 A1 12/2002 Manzo
2002/0188294 A1 12/2002 Couture et al.
2003/0078577 A1 4/2003 Truckai et al.
2003/0135204 A1 7/2003 Lee et al.
2003/0135205 A1 7/2003 Davenport et al.
2003/0144652 A1 7/2003 Baker et al.
2003/0171747 A1 9/2003 Kanehira et al.
2003/0181910 A1 9/2003 Dycus et al.
2004/0006340 A1 1/2004 Latterell et al.
2004/0049185 A1 3/2004 Latterell et al.
2004/0143263 A1 7/2004 Schechter et al.
2004/0232199 A1 11/2004 Shelton et al.
2004/0267310 A1 12/2004 Racenet et al.
2005/0006430 A1 1/2005 Wales
2005/0006434 A1 1/2005 Wales et al.
2005/0021027 A1 1/2005 Shields et al.
2005/0070925 A1 3/2005 Shelton et al.
2005/0070958 A1 3/2005 Swayze et al.
2005/0101991 A1 5/2005 Ahlberg et al.
2005/0113826 A1 5/2005 Johnson et al.
2005/0171533 A1 8/2005 Latterell et al.
2005/0178813 A1 8/2005 Swayze et al.
2005/0187576 A1 8/2005 Whitman et al.
2005/0273084 A1 12/2005 Hinman et al.
2005/0273085 A1 12/2005 Hinman et al.
2006/0000868 A1 1/2006 Shelton, IV et al.
2006/0016853 A1 1/2006 Racenet
2006/0020287 A1 1/2006 Lee et al.
2006/0022014 A1 2/2006 Shelton, IV et al.
2006/0022015 A1 2/2006 Shelton et al.
2006/0024817 A1 2/2006 Deguchi et al.
2006/0025809 A1 2/2006 Shelton, IV
2006/0025810 A1 2/2006 Shelton, IV
2006/0025811 A1 2/2006 Shelton, IV
2006/0025812 A1 2/2006 Shelton, IV
2006/0025813 A1 2/2006 Shelton et al.
2006/0025816 A1 2/2006 Shelton, IV
2006/0049230 A1 3/2006 Shelton, IV et al.
2006/0097026 A1 5/2006 Shelton, IV
2006/0111209 A1 5/2006 Hinman et al.
2006/0111210 A1 5/2006 Hinman
2006/0124689 A1 6/2006 Arad et al.
2006/0161190 A1 7/2006 Gadberry et al.
2006/0190031 A1 8/2006 Wales et al.
2006/0199999 A1 9/2006 Ikeda et al.
2006/0217706 A1 9/2006 Lau et al.
2006/0217709 A1 9/2006 Couture et al.
2006/0271042 A1 11/2006 Latterell et al.
2007/0010838 A1 1/2007 Shelton, IV et al.
2007/0045379 A1 3/2007 Shelton, IV
2007/0250113 A1 10/2007 Hegeman et al.
2007/0262116 A1 11/2007 Hueil et al.
2007/0270884 A1* 11/2007 Smith ................ A61B 17/1155 606/1
2008/0023522 A1* 1/2008 Olson .................. A61B 17/105 227/175.1
2008/0029577 A1 2/2008 Shelton et al.
2008/0064572 A1 3/2008 Nardone
2008/0065100 A1 3/2008 Larkin
2008/0078804 A1 4/2008 Shelton et al.
2008/0086114 A1 4/2008 Schmitz et al.
2008/0093517 A1 4/2008 Chen
2008/0108446 A1 5/2008 Faude
2008/0161174 A1 7/2008 Lo
2008/0196533 A1 8/2008 Bergamasco et al.
2008/0210738 A1 9/2008 Shelton et al.
2008/0280736 A1 11/2008 D'Eredita
2008/0305934 A1 12/2008 Medina
2008/0308607 A1 12/2008 Timm et al.
2009/0090763 A1* 4/2009 Zemlok ............ A61B 17/07207 227/175.2
2009/0181832 A1 7/2009 Bell
2009/0277947 A1 11/2009 Viola
2010/0006620 A1 1/2010 Sorrentino et al.
2010/0009818 A1 1/2010 Simonson et al.
2010/0057081 A1 3/2010 Hanna
2010/0057085 A1 3/2010 Holcomb et al.
2010/0076461 A1 3/2010 Viola et al.
2010/0076474 A1 3/2010 Yates et al.
2010/0096431 A1* 4/2010 Smith .................. A61B 17/115 227/175.2
2010/0108740 A1 5/2010 Pastorelli et al.
2010/0145334 A1 6/2010 Olson et al.
2010/0179545 A1 7/2010 Twomey et al.
2010/0198248 A1 8/2010 Vakharia
2010/0213240 A1* 8/2010 Kostrzewski ...... A61B 17/3209 227/180.1
2010/0331857 A1 12/2010 Doyle et al.
2011/0017801 A1* 1/2011 Zemlok ............ A61B 17/07207 227/175.1
2011/0022078 A1 1/2011 Hinman
2011/0036891 A1 2/2011 Zemlok et al.
2011/0087238 A1 4/2011 Wang et al.
2011/0118707 A1 5/2011 Burbank
2011/0118778 A1 5/2011 Burbank
2011/0121049 A1* 5/2011 Malinouskas .......... A61B 90/98 606/1
2011/0121050 A1 5/2011 Nicholas et al.
2011/0139851 A1* 6/2011 McCuen .......... A61B 17/07207 227/175.1
2011/0152879 A1 6/2011 Williams
2011/0174863 A1 7/2011 Shelton, IV et al.
2011/0186614 A1 8/2011 Kasvikis
2011/0204119 A1* 8/2011 McCuen .............. A61B 17/068 227/175.1
2011/0251612 A1 10/2011 Faller et al.
2011/0251613 A1 10/2011 Guerra et al.
2011/0282339 A1 11/2011 Weizman et al.
2011/0288573 A1 11/2011 Yates et al.
2011/0290851 A1 12/2011 Shelton, IV
2011/0290853 A1 12/2011 Shelton, IV et al.
2011/0290854 A1 12/2011 Timm et al.
2011/0290855 A1* 12/2011 Moore ................... A61B 34/30 227/176.1
2011/0295269 A1* 12/2011 Swensgard ........... A61B 34/76 606/130
2011/0295270 A1 12/2011 Giordano et al.
2011/0301603 A1 12/2011 Kerr et al.
2011/0319886 A1 12/2011 Chojin et al.
2012/0000962 A1 1/2012 Racenet et al.
2012/0022584 A1 1/2012 Donnigan et al.
2012/0071891 A1 3/2012 Itkowitz et al.
2012/0205419 A1 8/2012 Weir et al.
2012/0205421 A1* 8/2012 Shelton, IV ........... A61B 50/24 227/177.1
2012/0209253 A1 8/2012 Donhowe
2012/0223121 A1* 9/2012 Viola ............... A61B 17/07207 227/175.1
2012/0228358 A1 9/2012 Zemlok et al.
2012/0248167 A1 10/2012 Flanagan et al.
2012/0255986 A1 10/2012 Petty et al.
2012/0265241 A1 10/2012 Hart et al.
2012/0289999 A1 11/2012 Frank
2012/0298719 A1 11/2012 Shelton, IV et al.
2013/0015231 A1 1/2013 Kostrzewski
2013/0037597 A1* 2/2013 Katre ................. A61B 17/0686 227/176.1
2013/0046303 A1 2/2013 Evans et al.
2013/0056521 A1 3/2013 Swensgard
2013/0068821 A1 3/2013 Huitema et al.
2013/0075448 A1 3/2013 Schmid et al.
2013/0087599 A1 4/2013 Krumanaker et al.
2013/0098965 A1* 4/2013 Kostrzewski ........ A61B 17/072 227/176.1
2013/0098966 A1 4/2013 Kostrzewski et al.
2013/0116668 A1* 5/2013 Shelton, IV ........... A61B 34/30 606/1
2013/0126586 A1 5/2013 Zhang et al.
2013/0148577 A1 6/2013 Terry et al.

(56) References Cited

U.S. PATENT DOCUMENTS

2013/0240604 A1 9/2013 Knodel
2013/0248577 A1 9/2013 Leimbach et al.
2013/0256373 A1* 10/2013 Schmid ............ A61B 17/07207 227/176.1
2013/0277410 A1 10/2013 Fernandez et al.
2013/0282052 A1 10/2013 Aranyi et al.
2013/0296922 A1 11/2013 Allen, IV et al.
2013/0327808 A1 12/2013 Chen et al.
2014/0001236 A1 1/2014 Shelton, IV et al.
2014/0005653 A1 1/2014 Shelton, IV et al.
2014/0005654 A1 1/2014 Batross et al.
2014/0005662 A1 1/2014 Shelton, IV
2014/0005677 A1 1/2014 Shelton, IV et al.
2014/0021239 A1 1/2014 Kostrzewski
2014/0025071 A1 1/2014 Sims et al.
2014/0027492 A1 1/2014 Williams
2014/0100569 A1 4/2014 Lawes et al.
2014/0100600 A1 4/2014 Kendrick
2014/0103093 A1 4/2014 Koch, Jr. et al.
2014/0110455 A1* 4/2014 Ingmanson .......... A61B 17/072 227/176.1
2014/0128867 A1 5/2014 Collings et al.
2014/0131418 A1 5/2014 Kostrzewski
2014/0175152 A1 6/2014 Hess et al.
2014/0180286 A1 6/2014 Marczyk et al.
2014/0183244 A1* 7/2014 Duque ................. A61B 17/068 606/167
2014/0200596 A1 7/2014 Weir et al.
2014/0200612 A1 7/2014 Weir et al.
2014/0200851 A1 7/2014 Weir et al.
2014/0214049 A1 7/2014 Jeong et al.
2014/0239036 A1 8/2014 Zerkle et al.
2014/0239044 A1 8/2014 Hoffman
2014/0239046 A1* 8/2014 Milliman ......... A61B 17/07292 227/176.1
2014/0246477 A1 9/2014 Koch, Jr. et al.
2014/0249557 A1 9/2014 Koch, Jr. et al.
2014/0257331 A1 9/2014 Kim et al.
2014/0263546 A1 9/2014 Aranyi
2014/0263550 A1* 9/2014 Aranyi ............. A61B 17/07207 227/175.3
2014/0263552 A1* 9/2014 Hall ................... A61B 17/0686 227/176.1
2014/0263559 A1 9/2014 Williams et al.
2014/0263565 A1* 9/2014 Lytle, IV ............... A61B 17/32 227/180.1
2014/0263567 A1* 9/2014 Williams ......... A61B 17/07207 227/180.1
2014/0263569 A1* 9/2014 Williams ............. A61B 17/105 227/180.1
2014/0276731 A1 9/2014 Voegele et al.
2014/0276776 A1 9/2014 Parihar et al.
2014/0284372 A1 9/2014 Kostrzewski
2014/0305989 A1 10/2014 Parihar et al.
2014/0309666 A1 10/2014 Shelton, IV et al.
2014/0343550 A1 11/2014 Faller et al.
2014/0343569 A1 11/2014 Turner
2014/0364851 A1 12/2014 Batross et al.
2015/0018856 A1 1/2015 Poo et al.
2015/0073746 A1 3/2015 Gris et al.
2015/0088131 A1 3/2015 Weisshaupt et al.
2015/0141981 A1 5/2015 Price et al.
2015/0141993 A1 5/2015 Schechter et al.
2015/0173756 A1 6/2015 Baxter, III
2015/0173789 A1 6/2015 Baxter, III et al.
2015/0209030 A1 7/2015 Kostrzewski et al.
2015/0209037 A1 7/2015 Kostrzewski et al.
2015/0250530 A1 9/2015 Manzo et al.
2015/0256609 A1 9/2015 Morton et al.
2015/0272575 A1* 10/2015 Leimbach .............. A61B 90/96 227/175.3
2015/0272576 A1* 10/2015 Cappola ............... A61B 17/072 227/175.2
2015/0272583 A1* 10/2015 Leimbach ............... A61L 2/087 227/176.1
2015/0272606 A1 10/2015 Nobis
2015/0297227 A1 10/2015 Huitema et al.
2015/0297230 A1* 10/2015 Schellin ............... A61B 17/072 227/176.1
2015/0297235 A1 10/2015 Harris et al.
2015/0316431 A1 11/2015 Collins et al.
2015/0369277 A1 12/2015 Fevre et al.
2015/0374396 A1 12/2015 Strobl et al.
2016/0038227 A1 2/2016 Garrison
2016/0058441 A1 3/2016 Morgan et al.
2016/0058450 A1 3/2016 Shelton, IV et al.
2016/0066916 A1 3/2016 Overmyer et al.
2016/0089148 A1 3/2016 Harris et al.
2016/0120544 A1 5/2016 Shelton, IV et al.
2016/0157863 A1 6/2016 Williams et al.
2016/0157926 A1 6/2016 Boudreaux
2016/0166256 A1 6/2016 Baxter, III et al.
2016/0174973 A1 6/2016 Shelton, IV et al.
2016/0174977 A1 6/2016 Lytle, IV et al.
2016/0175033 A1 6/2016 Le
2016/0192999 A1 7/2016 Stulen et al.
2016/0199124 A1 7/2016 Thomas et al.
2016/0235473 A1 8/2016 Hagland
2016/0235489 A1 8/2016 Gombert et al.
2016/0242782 A1 8/2016 Shelton, IV et al.
2016/0249921 A1 9/2016 Cappola et al.
2016/0270780 A1 9/2016 Hall et al.
2016/0287251 A1 10/2016 Shelton, IV et al.
2016/0287316 A1 10/2016 Worrell et al.
2016/0296226 A1 10/2016 Kostrzewski
2016/0317216 A1 11/2016 Hermes et al.
2016/0338764 A1 11/2016 Krastins et al.
2016/0345971 A1 12/2016 Bucciaglia et al.
2016/0374672 A1* 12/2016 Bear ......................... H02J 7/00 606/219
2016/0374673 A1* 12/2016 Stager .................. A61B 17/068 227/176.1
2017/0010578 A1 1/2017 Miyakawa
2017/0042604 A1 2/2017 McFarland et al.
2017/0055981 A1* 3/2017 Vendely ........... A61B 17/07292
2017/0056098 A1 3/2017 Crews et al.
2017/0065331 A1 3/2017 Mayer et al.
2017/0079710 A1 3/2017 Deville et al.
2017/0097035 A1 4/2017 Zimmerman et al.
2017/0105754 A1 4/2017 Boudreaux et al.
2017/0135746 A1 5/2017 Tetzlaff et al.
2017/0143335 A1* 5/2017 Gupta .............. A61B 17/07207
2017/0156788 A1 6/2017 Johnson et al.
2017/0189028 A1 7/2017 Aranyi
2017/0202605 A1 7/2017 Shelton, IV et al.
2017/0231853 A1 8/2017 Kapadia
2017/0245857 A1 8/2017 Shelton, IV et al.
2017/0265865 A1 9/2017 Burbank
2017/0290584 A1 10/2017 Jasemian et al.
2017/0296172 A1 10/2017 Harris et al.
2017/0296173 A1 10/2017 Shelton, IV et al.
2017/0296183 A1* 10/2017 Shelton, IV ..... A61B 17/07207
2018/0008265 A1 1/2018 Hatanaka et al.
2018/0021042 A1 1/2018 Nicholas et al.
2018/0078268 A1 3/2018 Messerly et al.
2018/0125570 A1 5/2018 Rioux
2018/0161052 A1 6/2018 Weir et al.
2018/0168581 A1 6/2018 Hunter et al.
2018/0168585 A1 6/2018 Shelton, IV et al.
2018/0168620 A1 6/2018 Huang et al.
2018/0168622 A1* 6/2018 Shelton, IV ..... A61B 17/07207
2018/0168628 A1* 6/2018 Hunter ............... A61B 17/0682
2018/0168637 A1* 6/2018 Harris .................. A61B 17/072
2018/0168641 A1* 6/2018 Harris .................... A61B 90/03
2018/0168642 A1 6/2018 Shelton, IV et al.
2018/0168644 A1* 6/2018 Shelton, IV ........... A61B 90/03
2018/0168649 A1 6/2018 Shelton, IV et al.
2018/0168650 A1 6/2018 Shelton, IV et al.
2018/0206844 A1 7/2018 Harris et al.
2018/0214200 A1 8/2018 Nanditale et al.
2018/0232951 A1 8/2018 Alterovitz et al.
2018/0250085 A1 9/2018 Simi et al.

(56) References Cited

U.S. PATENT DOCUMENTS

2018/0296213 A1 10/2018 Strobl
2018/0310935 A1 11/2018 Wixey
2018/0310948 A1 11/2018 Stamm et al.
2018/0317915 A1 11/2018 McDonald, II
2018/0353186 A1* 12/2018 Mozdzierz ..... A61B 17/320016
2019/0000454 A1 1/2019 Swayze et al.
2019/0000525 A1 1/2019 Messerly et al.
2019/0015124 A1 1/2019 Williams et al.
2019/0029746 A1 1/2019 Dudhedia et al.
2019/0059894 A1 2/2019 Kumada et al.
2019/0076143 A1 3/2019 Smith
2019/0083086 A1 3/2019 Klaffenböck et al.
2019/0083819 A1 3/2019 Mitchell et al.
2019/0099181 A1 4/2019 Shelton, IV et al.
2019/0125347 A1 5/2019 Stokes et al.
2019/0133571 A1 5/2019 Racenet et al.
2019/0142531 A1 5/2019 Wentworth et al.
2019/0150919 A1 5/2019 Williams et al.
2019/0192137 A1 6/2019 Shelton, IV et al.
2019/0201146 A1 7/2019 Shelton, IV et al.
2019/0231350 A1 8/2019 Scott et al.
2019/0239881 A1 8/2019 Laurent et al.
2019/0282233 A1* 9/2019 Burbank .......... A61B 17/07207
2019/0290374 A1 9/2019 Ramadorai
2019/0298346 A1* 10/2019 Shelton, IV ..... A61B 17/07207
2019/0298354 A1* 10/2019 Shelton, IV ........... A61B 17/34
2019/0298355 A1 10/2019 Shelton, IV et al.
2019/0298356 A1 10/2019 Shelton, IV et al.
2019/0314107 A1 10/2019 Worrell et al.
2019/0365458 A1 12/2019 Whitlock et al.
2020/0054338 A1 2/2020 Shen
2020/0205811 A1* 7/2020 Posey .................. A61B 17/072
2020/0214706 A1* 7/2020 Vendely ................ A61B 17/08
2020/0305872 A1 10/2020 Weidner et al.
2020/0397430 A1* 12/2020 Patel .................... A61B 17/072
2021/0000557 A1 1/2021 Mustufa et al.
2021/0059670 A1* 3/2021 Overmyer ........ A61B 17/07207
2021/0153927 A1 5/2021 Ross et al.
2021/0161529 A1 6/2021 Wixey
2021/0177412 A1 6/2021 Wilson et al.
2021/0177495 A1 6/2021 Ross et al.
2021/0177500 A1 6/2021 Khalaji
2021/0186494 A1 6/2021 Shelton, IV et al.
2021/0196350 A1 7/2021 Fiebig et al.
2021/0236119 A1* 8/2021 Chavan ................ A61B 17/072
2021/0267596 A1 9/2021 Fanelli et al.
2021/0290232 A1 9/2021 Harris et al.
2021/0290233 A1 9/2021 Shelton, IV et al.
2021/0386427 A1 12/2021 Millman et al.
2022/0015762 A1* 1/2022 Wixey ................... A61B 90/90
2022/0015763 A1* 1/2022 Wixey ................... A61B 90/08
2022/0015823 A1 1/2022 Wilson et al.
2022/0031346 A1 2/2022 Parks
2022/0054130 A1 2/2022 Overmyer et al.
2022/0061836 A1 3/2022 Parihar et al.
2022/0061840 A1 3/2022 Hites
2022/0061841 A1 3/2022 Wixey et al.
2022/0071632 A1 3/2022 Patel et al.
2022/0079585 A1 3/2022 Egan
2022/0125428 A1 4/2022 Ragosta et al.
2022/0142642 A1 5/2022 De et al.
2022/0160358 A1 5/2022 Wixey
2022/0167985 A1* 6/2022 George ............ A61B 17/07207
2022/0183686 A1 6/2022 Wixey et al.
2022/0192665 A1 6/2022 Wellman
2022/0218344 A1* 7/2022 Leimbach ................. A61L 2/07
2022/0296243 A1 9/2022 Nalagatla et al.
2022/0304691 A1 9/2022 Fernandes et al.
2022/0346790 A1 11/2022 Wellman
2022/0378537 A1 12/2022 Hites et al.
2022/0387027 A1 12/2022 Shelton, IV et al.
2022/0395270 A1 12/2022 Patel et al.
2023/0020577 A1 1/2023 Kerver et al.
2023/0047784 A1 2/2023 Patel et al.
2023/0052074 A1 2/2023 Wixey
2023/0099430 A1* 3/2023 Schings ........... A61B 17/07207 227/175.2
2023/0101993 A1* 3/2023 Baril ................ A61B 17/07207 227/175.4
2023/0120209 A1 4/2023 Parks et al.
2023/0210527 A1* 7/2023 Shelton, IV ..... A61B 17/07207 227/175.4
2023/0225731 A1 7/2023 Burbank
2023/0329711 A1 10/2023 Wixey et al.
2024/0023961 A1 1/2024 Wixey et al.
2024/0081824 A1 3/2024 Hites
2024/0108343 A1 4/2024 Wixey
2024/0138834 A1 5/2024 Wellman
2024/0252171 A1 8/2024 Wixey et al.
2024/0260959 A1 8/2024 Wixey et al.
2024/0293122 A1 9/2024 Wixey
2024/0315761 A1 9/2024 Whitlock et al.
2024/0335194 A1 10/2024 Patel et al.
2024/0341766 A1 10/2024 Millman et al.
2024/0350143 A1 10/2024 Yee et al.
2024/0407782 A1 12/2024 Patel et al.
2025/0040930 A1 2/2025 Wellman

FOREIGN PATENT DOCUMENTS

CN 104042275 A 9/2014
CN 105007836 A 10/2015
CN 105769331 A 7/2016
CN 106232026 A 12/2016
CN 106491203 A 3/2017
CN 107920819 A 4/2018
CN 108024809 A 5/2018
CN 112165909 A 1/2021
DE 694747 C 8/1940
DE 3724525 C1 5/1988
DE 102012103503 A1 10/2013
EP 0277532 B1 8/1990
EP 0469396 A1 2/1992
EP 0277529 B1 4/1993
EP 0641546 A1 3/1995
EP 0986336 A1 3/2000
EP 1090592 A1 4/2001
EP 1479348 A1 * 11/2004 ....... A61B 17/07207
EP 1728473 A1 12/2006
EP 1479346 B1 1/2007
EP 1621141-81 7/2007
EP 2374419 A2 10/2011
EP 1316290 B1 2/2012
EP 2517639 A1 10/2012
EP 2540231 A2 1/2013
EP 1754445-81 10/2013
EP 2777529 A1 9/2014
EP 2777530 A1 9/2014
EP 2777532 A2 9/2014
EP 2777535 A1 * 9/2014 ........... A61B 17/068
EP 2779921 A2 9/2014
EP 2932918 A1 10/2015
EP 2944275 A2 11/2015
EP 2992834 A1 3/2016
EP 2992849 A1 3/2016
EP 3000408 A2 3/2016
EP 3120780 A2 1/2017
EP 3135225 A2 3/2017
EP 3158947 A1 4/2017
EP 3173029 A1 5/2017
EP 3205291 A1 8/2017
EP 3338703 A1 6/2018
EP 2992834 B1 * 12/2018 ....... A61B 17/07207
EP 3498190 A1 6/2019
EP 3756567 A1 12/2020
FR 2828952 B1 12/2005
JP S5794132 A 6/1982
JP 2001170069 A 6/2001
JP 5301166 B2 9/2013
JP 2014530653 A 11/2014
JP 2016508792 A 3/2016
JP 2016513570 A 5/2016
JP 2017500146 A 1/2017
JP 2017513564 A 6/2017

(56) References Cited

FOREIGN PATENT DOCUMENTS

| | | | |
|---|---|---|---|
| JP | 2017527396 | A | 9/2017 |
| JP | 6411461 | B2 | 10/2018 |
| JP | 2019141659 | A | 8/2019 |
| SU | 405234 | A1 | 9/1975 |
| SU | 886900 | A1 | 12/1981 |
| SU | 1333319 | A2 | 8/1987 |
| SU | 1442191 | A1 | 12/1988 |
| SU | 1459659 | A1 | 2/1989 |
| WO | WO-8602254 | A1 | 4/1986 |
| WO | WO-9005489 | A1 | 5/1990 |
| WO | WO-9734533 | A1 | 9/1997 |
| WO | WO-03094743 | A1 | 11/2003 |
| WO | WO-03094746 | A1 | 11/2003 |
| WO | WO-03094747 | A1 | 11/2003 |
| WO | WO-2004020859 | A1 | 3/2004 |
| WO | WO-2009112802 | A1 | 9/2009 |
| WO | WO-2012142872 | A1 | 10/2012 |
| WO | WO-2014106275 | A1 | 7/2014 |
| WO | WO-2016073538 | A1 | 5/2016 |
| WO | WO-2017026141 | A1 | 2/2017 |
| WO | WO-2017034803 | A2 | 3/2017 |
| WO | WO-2017156070 | A1 | 9/2017 |
| WO | WO-2017214243 | A1 | 12/2017 |
| WO | WO-2018005750 | A1 | 1/2018 |
| WO | WO-2018071497 | A1 | 4/2018 |
| WO | WO-2018118402 | A1 | 6/2018 |
| WO | WO-2019090047 | A1 | 5/2019 |
| WO | WO-2020081960 | A1 | 4/2020 |
| WO | WO-2020131685 | A1 | 6/2020 |
| WO | WO-2020131692 | A1 | 6/2020 |
| WO | WO-2022150215 | A1 | 7/2022 |
| WO | WO-2022200951 | A1 | 9/2022 |

OTHER PUBLICATIONS

International Search Report and Written Opinion for Application No. PCT/US2016/059527, mailed on Feb. 16, 2017, 13 pages (ISRG07220/PCT).
Nicholson, C., et al., "Plane Bearings," ESC Report, BSA Educational Services Committee, Oct. 1994, vol. 5(1), 02 pages.
European Search Report (Corrected version) for Application No. EP19750317.0, mailed on Mar. 28, 2022, 26 pages.
International Search Report and Written Opinion for Application No. PCT/US2020/054568. mailed Jan. 29, 2021, 13 pages.
International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US2020/025655, mailed Jul. 22, 2020, 8 pages.
International Search Report and Written Opinion for Application No. PCT/US19/17646, mailed on Apr. 16, 2019, 11 pages.
International Search Report and Written Opinion for Application No. PCT/US2019/019501. mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US2020/020672, mailed Jun. 29, 2020, 10 pages.
International Search Report and Written Opinion for Application No. PCT/US2020/033481, mailed Sep. 3, 2020, 22 pages.
International Search Report and Written Opinion for Application No. PCT/US2021/012284 mailed May 6, 2021, 23 pages.
International Search Report and Written Opinion for Application No. PCT/US2021/065308, mailed Apr. 21, 2022. 13 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
Vertut. J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Search Report and Written Opinion for Application No. PCT/US2021/065544, mailed Jun. 2, 2022, 21 pages.
Anonymous: "Slip Joint Pliers—Wikipedia," Sep. 2017, 1 Pages. Retrieved from internet URL:https://en.wikipedia.org/w/index.php?tilte=split_joint_pliers&oldid=801407143.
Burstein M.D., "8 MM Sureform 30 Staplers and Reloads," Sages, Jun. 2022, 1 Page. Retrieved from internet URL: https://www.accessdata.fda.gov/cdrh_docs/pdf21/K211997.pdf.
Extended European Search Report for Application No. EP18823002.3 mailed on Mar. 5, 2021,11 pages.
Extended European Search Report for Application No. EP19757451.0, mailed on May 19, 2022, 16 pages.
Extended European Search Report for Application No. EP19898247.2, mailed on Jan. 10, 2023, 12 pages.
Extended European Search Report for Application No. EP19900059.7, mailed on Dec. 5, 2022. 10 pages.
Extended European Search Report for Application No. EP20790773.4, mailed on Nov. 29, 2022, 09 pages.
Extended European Search Report for Application No. EP20815112.6, mailed on Jan. 5, 2023, 11 pages.
Extended European Search Report for Application No. EP20875978.7, mailed on Jan. 31, 2024, 26 pages.
Extended European Search Report for Application No. EP24155564.8, mailed on Jul. 8, 2024, 12 pages.
International Search Report and Written Opinion for Application No. PCT/US2018/039912, mailed on Oct. 12, 2018, 15 pages (ISRG08630/PCT).
Jaggi A., "8 mm SureForm 30 Curved-Tip Stapler, 8 mm SureForm 30 Stapler, SureForm 30 Reloads," U.S Food & Drug Administration, Dec. 2021, 11 pages. Retrieved from the internet URL:https://www.sages.org/publications/tavac/8-mm-sureform-30-staplers-and-reloads/.
International Search Report and Written Opinion for Application No. PCT/US2024/026826, mailed Jul. 26, 2024, 15 pages.

* cited by examiner

SURGICAL STAPLING INSTRUMENTS

CROSS REFERENCE TO RELATED APPLICATIONS

This application is the National Stage of International Application No. PCT/US2021/065544, which claims benefit of U.S. Provisional Application No. 63/134,962, filed Jan. 8, 2021, the entire disclosure of which is incorporated herein by reference for all purposes.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms. A surgical instrument is mounted on each of the robotic arms. Operative communication between master controllers and associated robotic arm and instrument assemblies is typically achieved through a control system. The control system typically includes at least one processor that relays input commands from the master controllers to the associated robotic arm and instrument assemblies and back in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912, 6,758,843, 6,246,200, and 5,800,423, the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. Nos. 6,702,805, 6,676,669, 5,855,583, 5,808,665, 5,445,166, and 5,184,601, the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide two or three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical instruments are often deployed into restrictive body cavities (e.g., through a cannula to inside the pelvis). Accordingly, it is desirable for the surgical instrument to be both compact and maneuverable for best access to and visibility of the surgical site. Known surgical instruments, however, may fail to be both compact and maneuverable. For example, known surgical instruments may lack maneuverability with respect to multiple degrees of freedom (e.g., roll, pitch, and yaw) and associated desired ranges of motion.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting devices, including known surgical staplers, have opposing jaws that clamp tissue and an articulated knife to cut the clamped tissue.

Many surgical clamping and cutting instruments include an instrument shaft supporting an end effector to which a replaceable stapler cartridge is mounted. An actuation mechanism articulates the stapler cartridge to deploy staples from the stapler cartridge to staple tissue clamped between the stapler cartridge and an articulable jaw of the end effector. Different types of stapler cartridges (or reloads) can be used that have different staple lengths suitable for different tissues to be stapled.

The use of replaceable stapler cartridges does, however, give rise to some additional issues. For example, prior to use, a suitable stapler cartridge having the correct staple length for the desired application should be mounted to the end effector. If a stapler cartridge having an unsuitable staple length is mistakenly mounted to the end effector, the result may be suboptimal if the error is not detected and corrected prior to stapling of the tissue. As another example, if a previously used stapler cartridge is not replaced with a suitable new stapler cartridge, the tissue clamped between the previously used stapler cartridge and the articulable jaw cannot be stapled due to the lack of staples to deploy. A similar problem can arise if a stapler cartridge is not mounted to the end effector prior to its use in the patient.

The potential disadvantages of firing a surgical stapling instrument while a spent stapler cartridge remains in place on the jaw has given rise to the development of various lockout mechanisms. However, incorporating conventional lockout features typically increases the diameter of the end effector, increasing overall instrument size and making a given instrument less ideal for minimally invasive surgery.

Other complications have arisen with the smaller surgical stapling instruments. One such complication is that as the staple cartridges and surgical instruments have grown smaller, the staples have been moved closer to the line of tissue dissection. Thus, the amount of tissue remaining between the inner-most row of staples and the line of dissection (sometimes referred to as the "tissue cuff") has been correspondingly reduced. This reduction in the width of the tissue cuff can result in frayed, ragged or torn tissue that does not adequately hold the staples. In addition, it can cause deformation of the inner-most row of staples, resulting in a suboptimal sealing of tissue.

Another complication arising from the continuously diminishing sizes of stapling instruments is that the increasingly tight engineering tolerances between the various components of the instrument have become more difficult to meet. Failure to adequately meet the engineering tolerances can result in various performance failures of the device. In particular, failure to meet tolerances between the jaws of the stapling instrument and the stapling cartridge can cause some of the components, such as the lockout mechanism, to either completely fail or to not function optimally. This can potentially cause tissue damage and/or unnecessary delays in the surgical procedure.

Accordingly, while the new telesurgical systems and devices have proven highly effective and advantageous, still further improvements would be desirable to overcome the drawbacks with existing instruments. The systems and devices described herein address these and other needs.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

Surgical stapling instruments and removable staple cartridges for use with those instruments are provided herein. The instruments and staple cartridges include mechanisms for identifying and/or deactivating the stapler cartridges. The stapling instrument includes a drive member for actuating the staple cartridge and a locking member movable from a disabled position permitting distal translation of the drive member through a staple firing stroke, to a locking position inhibiting distal translation of the drive member through the staple firing stroke. The staple cartridge may include a switch, pin or other mechanism for maintaining the locking member in the disabled position. The switch may be further configured to operate as a reload detection mechanism for determining the type of reload present in the surgical stapling instrument.

One of the advantages of the devices disclosed herein is that the switch can be configured to maintain the locking member in the disabled position and thus allow distal translation of the drive member to actuate the staples when the staple cartridge is fresh (i.e., not having been already fired). On the other hand, the switch can be configured to allow the locking member to move into the locking position during actuation of the staples (i.e., as the drive member is translated distally through the end effector). This effectively locks the instrument such that it cannot actuate a stapler cartridge that has already been fired.

In one aspect, a staple cartridge for use with the surgical instrument comprises a housing having at least one row of staple pockets for receiving staples therein and a channel for receiving the drive member of the surgical instrument. The cartridge further includes a switch defining proximal and distal ends and having one or more contact surface(s) at least partially disposed within the channel such that the drive member contacts the contact surface(s) as the drive member translates through the channel. The contact surface(s) extend transversely into the channel at an angle of less than about 45 degrees with the longitudinal axis of the cartridge, preferably less than about 30 degrees. This increases the time and distance in which the drive member contacts the switch as the drive member translates through the channel (referred to as "switch stroke").

Increasing the overall stroke of the switch as the drive member translates through the staple cartridge mitigates issues that may be caused by insufficient switch stroke. For example, an increased switch stroke ensures that the switch will move laterally out of the path of the drive member during distal translation of the drive member, thereby enabling the locking member. In addition, this ensures that the drive member will not get stuck on the switch as it is retracted proximally (i.e., if the switch has not been moved sufficiently outside of the channel during distal translation of the drive member). The drive member closes the jaws and drives staples into tissue as it is advanced distally through the end effector and then opens the jaws as it is retracted proximally. Thus, if the drive member were to get stuck during the proximal retraction, the jaws of the instrument would not completely open and the instrument could become stuck to the tissue, resulting in potential tissue damage and unnecessary delays in the procedure.

In certain embodiments, the switch may be configured to provide a detectable resistance upon engagement of the drive member with the contact surface in order to, for example, provide input for a reload detection mechanism that can detect: whether a stapler cartridge is mounted to the surgical instrument; whether the mounted stapler cartridge is unfired (or fresh) or has already been fired; and/or the type of the mounted stapler cartridge mounted to the end effector to ensure that the mounted stapler cartridge has a suitable staple length for the tissue to be stapled, based on the detectable resistance. Increasing the switch stroke ensures that this detection mechanism is more reliable.

The contact surface(s) may extend from a proximal end of the switch to a position at least about halfway to a midpoint between the proximal and distal ends of the switch. In certain embodiments, the contact surface(s) may extend to at least the midpoint between the proximal and distal ends of the switch.

In one such embodiment, the contact surface(s) comprise a first surface extending transversely into the channel and at least a second surface distal to the first surface and extending transversely into the channel from the first surface in a distal direction. The second surface defines a smaller angle with the longitudinal axis than the first surface. Thus, the second surface extends further in the longitudinal direction and therefore, provides a longer switch stroke for the drive member.

In another aspect, a staple cartridge for the surgical instrument comprises a housing having at least one row of staple pockets for receiving staples therein and a channel for receiving the drive member of the surgical instrument. The housing further comprises a proximal portion with an upper surface and a lateral slot. A switch is disposed within the lateral slot and has a contact surface at least partially disposed within the channel such that the drive member contacts the contact surface as the drive member translates through the channel. One or more protrusions or bumps extend from the upper surface of the proximal portion of the housing towards the first jaw of the surgical instrument.

The protrusions inhibit vertical movement of the proximal portion of the cartridge relative to the first upper jaw of the instrument. This stabilizes the proximal portion of the stable cartridge relative to the jaws of the instrument during actuation of the instrument and/or during reload detection.

Applicant has discovered that the drive member may create a torque against the switch and the proximal portion of the staple cartridge as it engages the switch. This torque can urge the proximal portion of the cartridge upwards toward the upper jaw. If there is any space between the jaw and the staple cartridge when the jaws are closed, this upward movement creates instability in the staple cartridge during actuation. The protrusions stabilize the proximal portion of the stapler cartridge by taking up any clearance and deforming against the jaw to the closed height between the jaw and the cartridge.

In certain embodiments, the protrusions extend from the upper surface of the proximal portion of the cartridge to a lower surface of the first jaw when the first and second jaws are in the closed positions. The one or more protrusions may comprise a deformable material and/or they may be shaped to deform upon the application of threshold level of force. In certain embodiments, the protrusions are configured to deform to the distance between the first jaw and the staple cartridge when the jaws are in the closed position to take up any clearance between the jaws and the staple cartridge.

In another aspect, a surgical instrument comprises an end effector having first and second jaws movable between open and closed positions. The second jaw comprises a cavity with upper surfaces on either side of the cavity facing the first jaw. A removable staple cartridge may be disposed within the cavity. The staple cartridge includes first and second rows of staple pockets and an upper tissue contacting surface. The upper tissue contacting surface includes first and second lateral portions overlying the first and second rows of staple pockets and a recessed portion between the first and second rows of staple pockets. The recessed portion of the tissue contacting surface is disposed below the upper surfaces of the second jaw.

In certain embodiments, the instrument further comprises a drive member having a cutting element configured to translate distally through a channel in the staple cartridge. The recessed portion of the tissue contacting surface overlies at least a portion of the channel. The recessed portion of the tissue contacting surface creates a jog in the plane in which the tissue sits between the jaws of the device, thereby increasing the length of the tissue contacting surfaces between the cutting element and the staples. This increases the width of the tissue cuff between the line of dissection and the stapled tissue, thereby minimizing deformation of the staples and fraying of tissue which results in a more optimal seal of the tissue.

In certain embodiments, the recessed portion of the tissue contacting surface extends from at least one lateral side of the channel to at least an opposite lateral side of the channel. The staple cartridge may further include one or more raised edges between each of the first and second rows of staple pockets and the recessed portion of the tissue contacting surface. The raised edges extend longitudinally along an upper surface of the housing and further increase the width of the tissue cuff between the line of tissue dissection and the staplers.

In certain embodiments, the stapler cartridge further comprises a switch having a contact surface at least partially disposed within the channel such that the drive member contacts the contact surface as the drive member translates through the channel. The drive member may be configured to contact the switch at an axial position of the drive member relative to the end effector. The switch may be configured to provide a detectable resistance upon engagement of the drive member at said axial position such that the type of stapler cartridge may be identified by a control unit.

The surgical instrument may be operatively coupled to the control unit, the control unit configured to process the detectable resistance to identify the stapler cartridge. The surgical instrument may further include an actuator configured to translate the drive member distally through the end effector. The actuator may include a control device of a robotic surgical system.

BRIEF DESCRIPTION OF THE DRAWINGS

The above and other aspects, features, and advantages of the present surgical instruments having a locking mechanism will become more apparent in light of the following detailed description when taken in conjunction with the accompanying drawings in which.

DETAILED DESCRIPTION

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail.

While the following description is presented with respect to a linear surgical stapler where staples are sequentially fired, it should be understood that features of the presently described surgical instruments may be readily adapted for use in any type of surgical clamping, cutting, ligating, dissecting, clipping, cauterizing, suturing and/or sealing instrument, whether or not the surgical instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. In addition, the features of the presently described surgical instruments may be readily adapted for may be readily adapted for use in other types of cartridges, such as linear and/or purse string stapler cartridges. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

The devices described herein may also be incorporated into a variety of different surgical instruments, such as those described in commonly-assigned, co-pending U.S. patent application Ser. Nos. 16/205,128, 16/427,427, 16/678,405, 16/904,482, 17/081,088 and 17/084,981 and International Patent Nos. PCT/US2019/107646, PCT/US2019/019501, PCT/US2019/062344, PCT/US2020/54568, PCT/US2019/064861, PCT/US2019/062768, PCT/2020/025655, PCT/US2020/056979, PCT/2019/066513, PCT/US2020/020672, PCT/US2019/066530 and PCT/US2020/033481, the complete disclosures of which are incorporated by reference herein in their entirety for all purposes as if copied and pasted herein.

Figure 1:
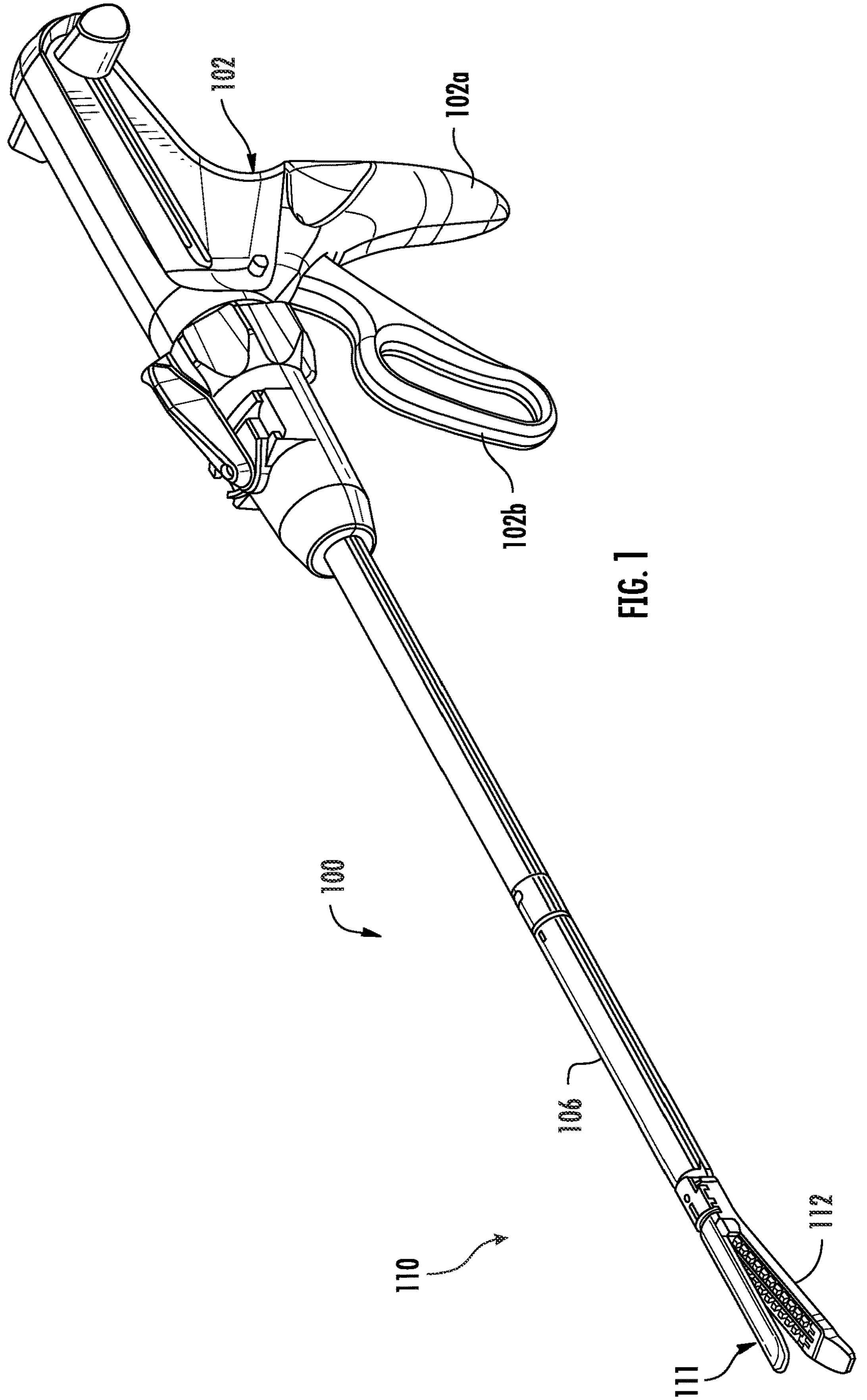
FIG. 1 is a perspective view of an illustrative surgical instrument having an end effector mounted to an elongated shaft, and an actuation mechanism.

FIG. 1 is a perspective view of an illustrative surgical instrument 100 having a handle assembly 102, and an end effector 110 mounted on an elongated shaft 106. End effector 110 includes a first and second jaws 111, 112. Handle assembly 102 includes a stationary handle 102*a* and a moveable handle 102*b* which serves as an actuator for surgical instrument 100.

Figure 1A:
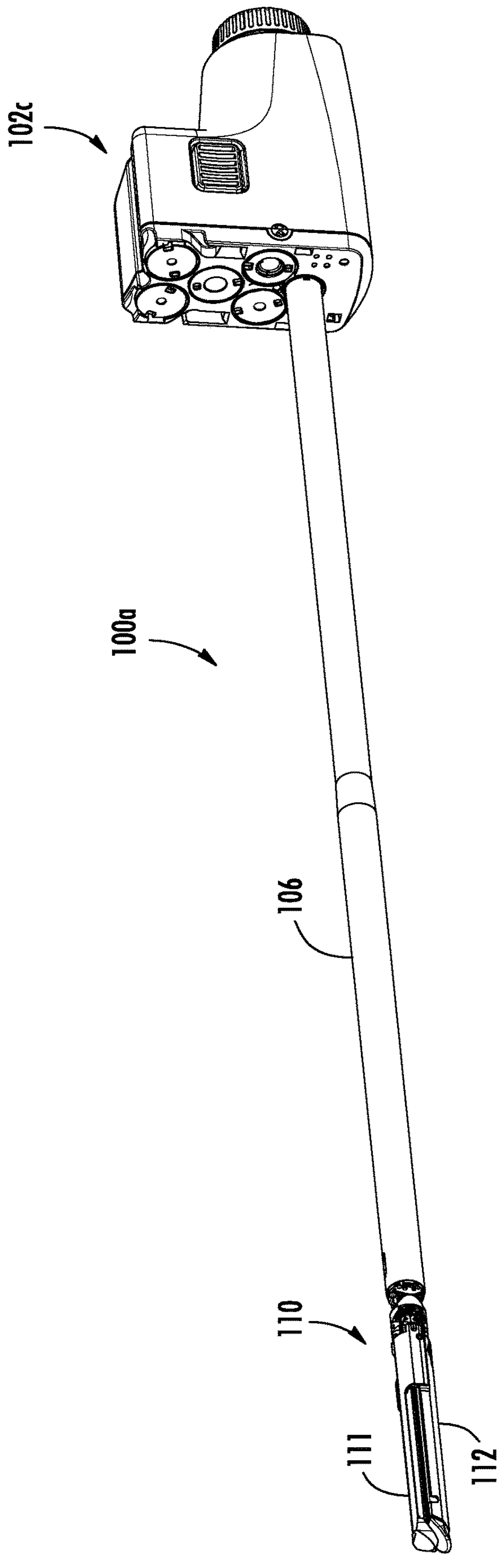
FIG. 1A is a perspective view of illustrative surgical instrument with a robotically controlled backend mechanism.

FIG. 1A illustrates a surgical instrument 100*a* that includes a backend mechanism 102*c* instead of the handle assembly shown in FIG. 1. Backend mechanism 102*c* typically provides a mechanical coupling between the drive tendons or cables of the instrument and motorized axes of the mechanical interface of a drive system. Further details of known backend mechanisms and surgical systems are described, for example, in U.S. Pat. Nos. 8,597,280, 7,048,745, and 10,016,244. Each of these patents is hereby incorporated by reference in its entirety.

The input couplers may interface with, and be driven by, corresponding output couplers (not shown) of a telesurgical surgery system, such as the system disclosed in U.S Pub. No. 2014/0183244A1, the entire disclosure of which is incorporated by reference herein. The input couplers are drivingly coupled with one or more input members (not shown) that are disposed within the instrument shaft 106. The input members are drivingly coupled with the end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and 10,016,244. Each of these patents is hereby incorporated by reference in its entirety for all purposes.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 2:
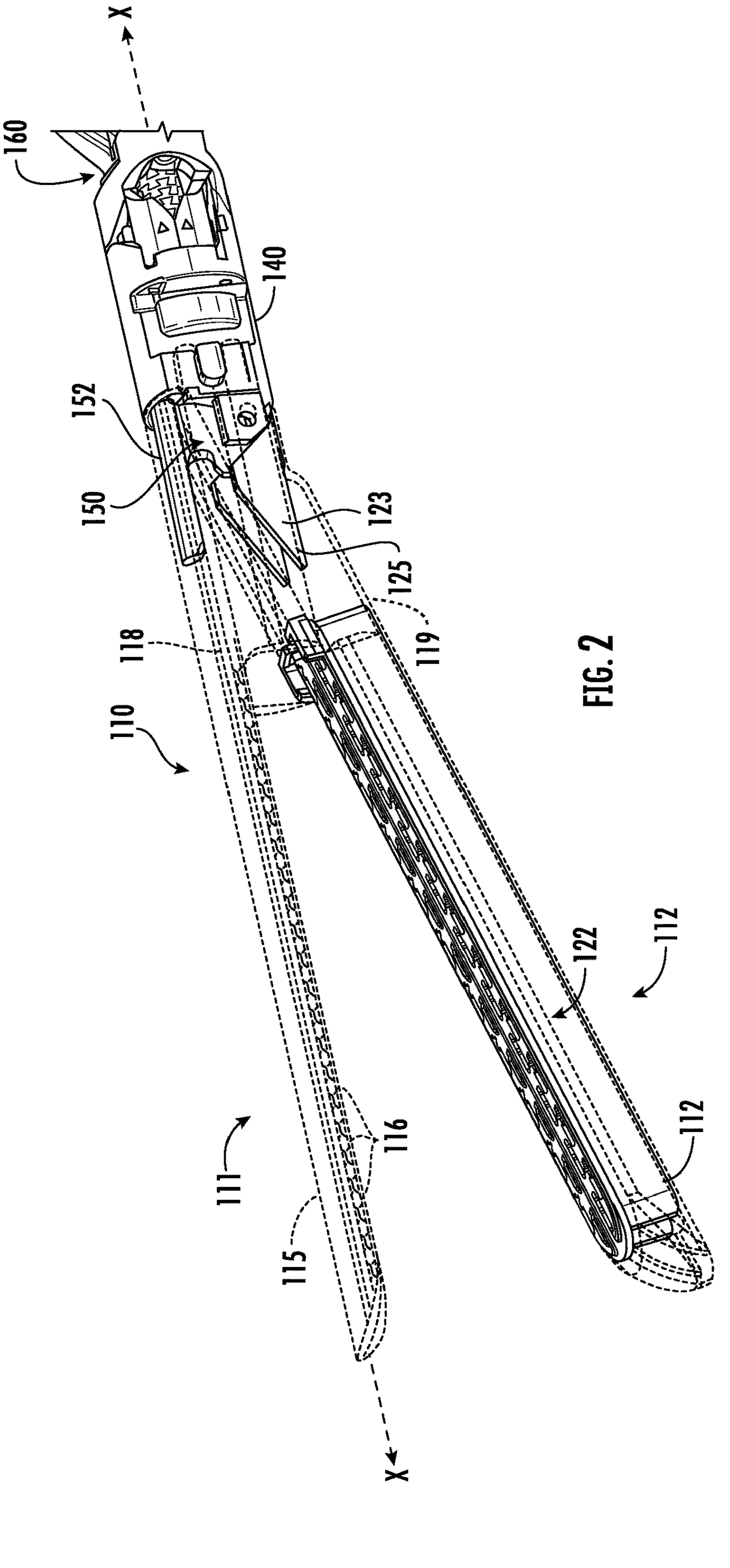
FIG. 2 is a perspective view of the distal end portion of an illustrative surgical instrument with the jaws in the open position.

FIG. 2 shows the distal end portion of surgical instrument 100, including an end effector 110 defining a longitudinal axis X-X and having a first jaw 111, a second jaw 112, a clevis 140 for mounting jaws 111, 112 to the instrument, and an articulation mechanism, such as a wrist assembly 160. In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. In the exemplary embodiment, first jaw 112 is a movable jaw 112 configured to move from an open position to a closed position relative to stationary jaw 111. First jaw 111 includes an anvil 115 having staple-forming pockets 116. In the open position, an unused stapler cartridge 122 (sometimes referred to as a fresh or unfired reload) can be loaded into movable jaw 112 and tissue may be positioned between the jaws 111, 112. In the closed position, jaws 111, 112 cooperate to clamp tissue such that stapler cartridge 122 and the anvil 115 are in close cooperative alignment.

Figure 3:
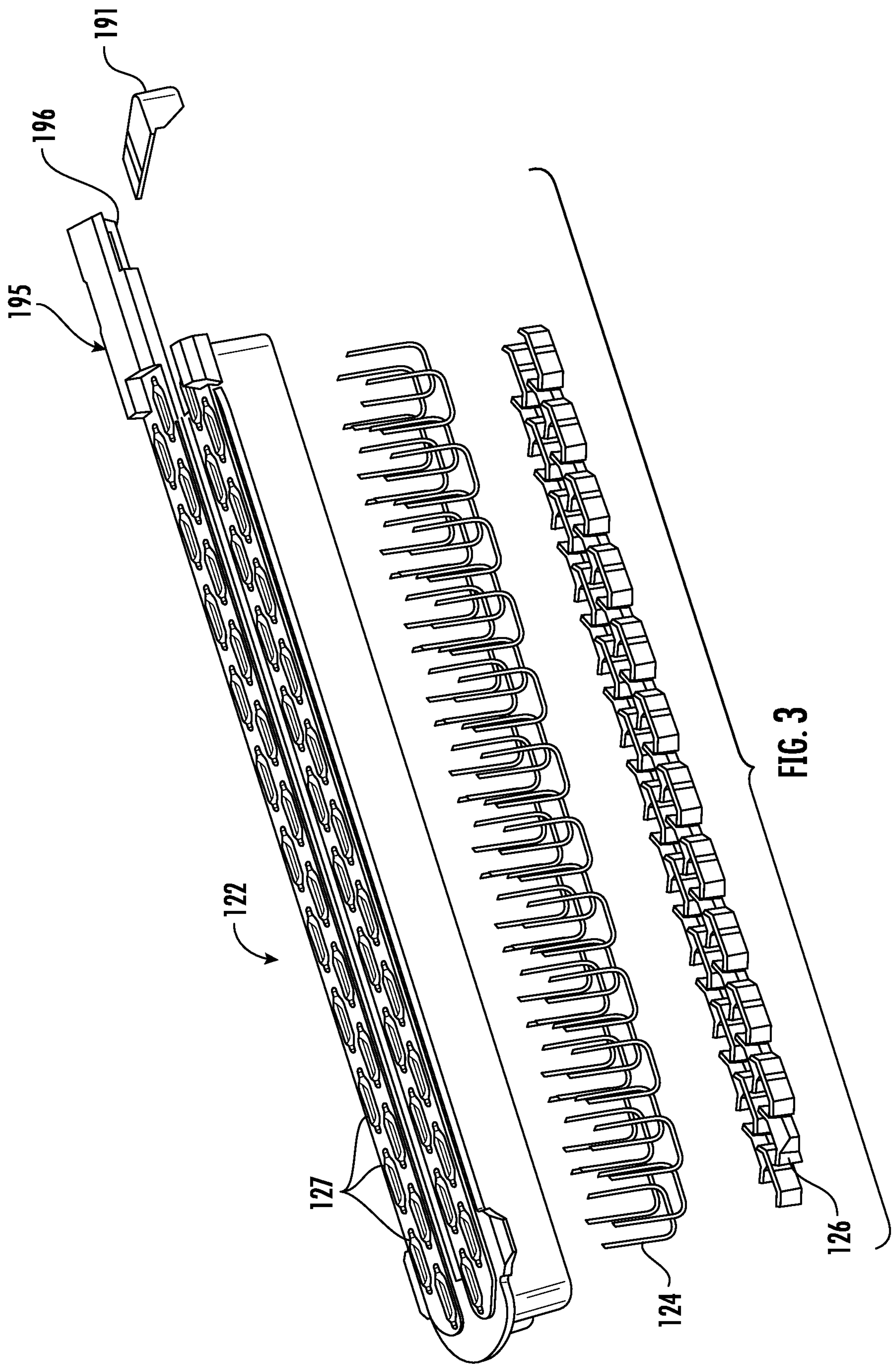
FIG. 3 is an exploded view of a cartridge configured for use with the surgical instrument of FIG. 1 including surgical fasteners, staple drivers, and a switch.

As shown in FIG. 3, stapler cartridge 122 may include a plurality of staples 124 supported on corresponding staple drivers 126 provided within respective staple retention openings or pockets 127 formed in stapler cartridge 122. In embodiments, stapler cartridge 122 further includes one or more switches 191 configured to engage a slot 196 formed on the proximal tail 195 of stapler cartridge 122. The functionality of switches 191 will be described in more detail below.

Referring again to FIG. 2, surgical instrument 100 may also include a drive member 150 configured to translate distally and retract proximally through the end effector 110. Drive member 150 may have a shuttle 123 integrally formed thereon including an inclined distal portion 125 that sequentially acts on staple drivers 126 upon distal movement of the drive member 150, camming staple drivers 126 upwardly, thereby moving staples 124 into deforming contact with anvil 115. In certain embodiments, shuttle 123 may be included within stapler cartridge 122 as a separate component. Drive member 150 includes an upper shoe 152 that is substantially aligned with and translates through a channel 118 in fixed jaw 111, while a lower shoe 154 (see FIG. 11) of drive member 150 translates through and underneath jaw 112. The details of the drive member and actuation will be described below.

Figure 4:
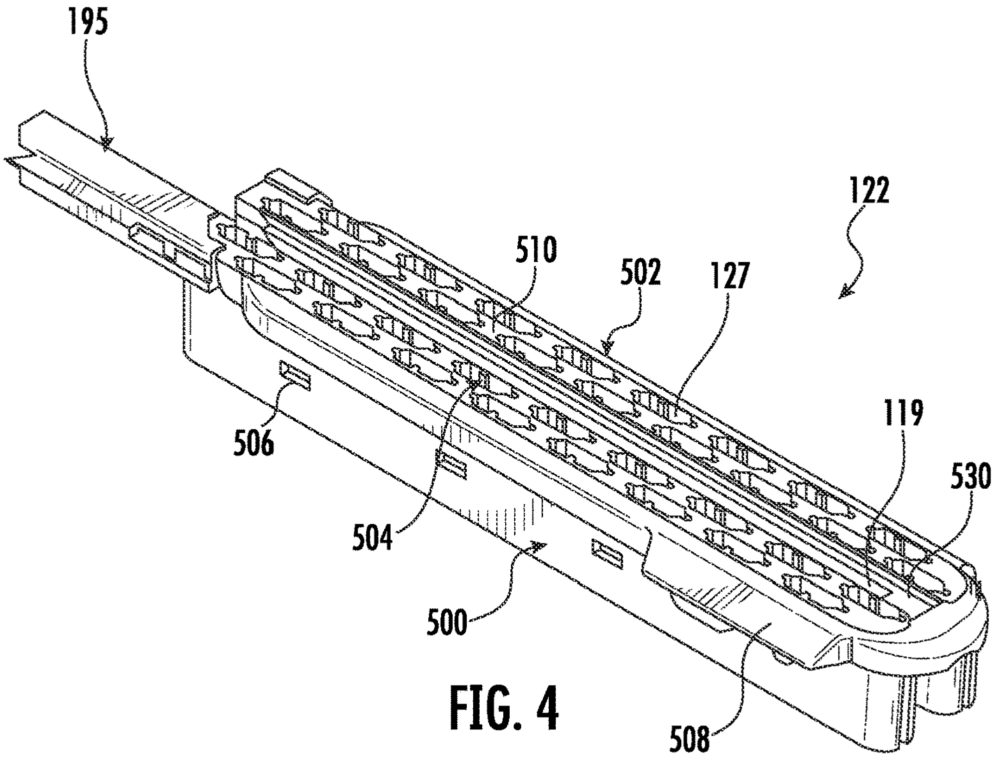
FIG. 4 is a perspective view of a stapler cartridge.
Figure 5:
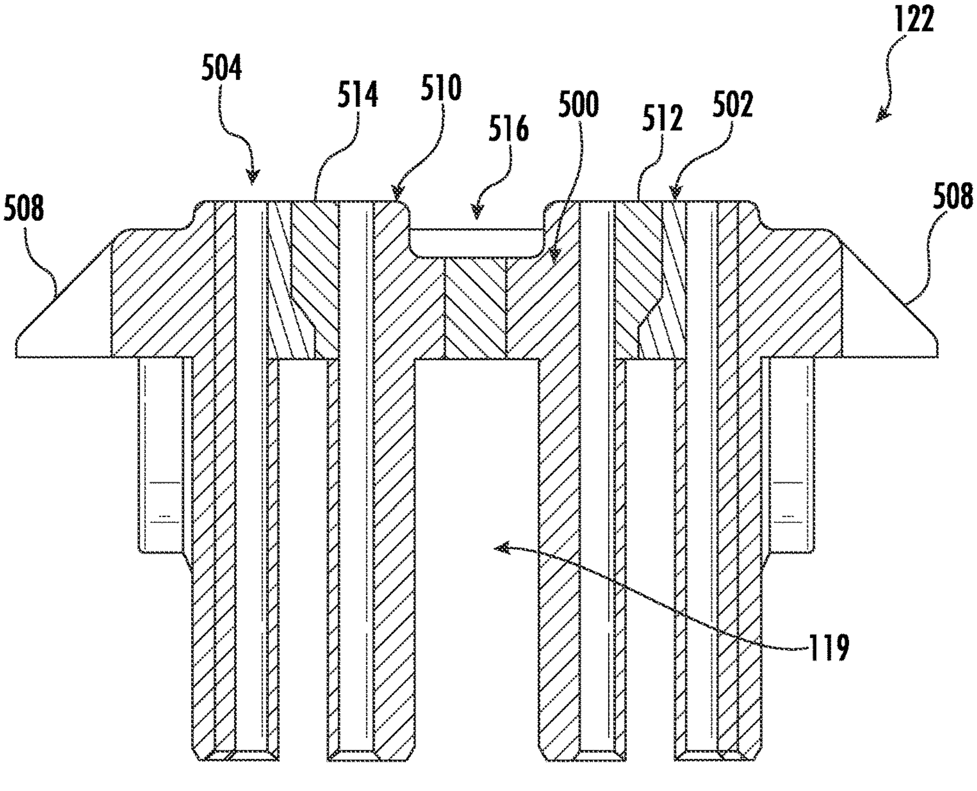
FIG. 5 is a cross-sectional view of the stapler cartridge of FIG. 4.
Figure 6:
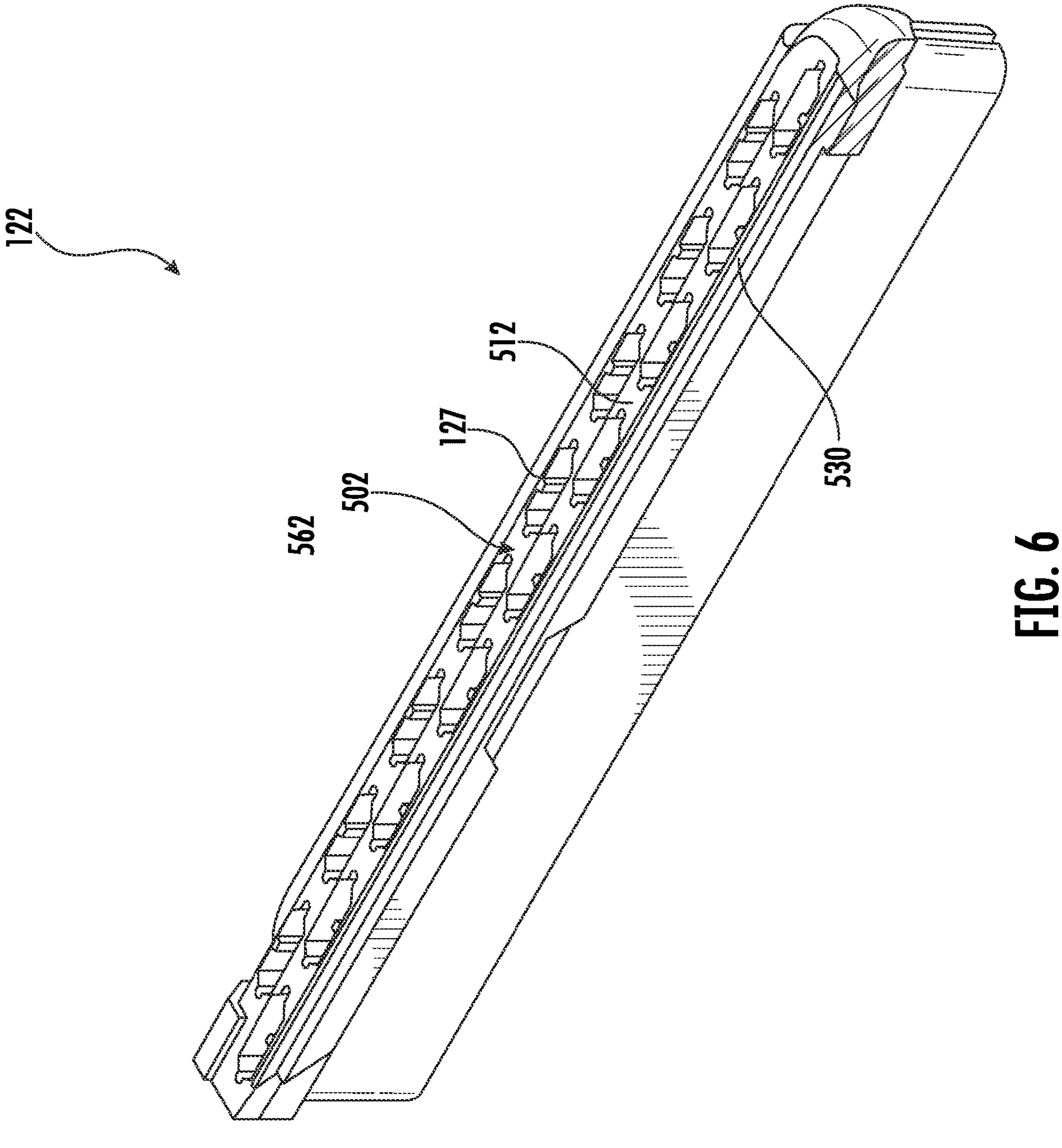
FIG. 6 is a perspective view of one side of the stapler cartridge of FIG. 4.
Figure 12:
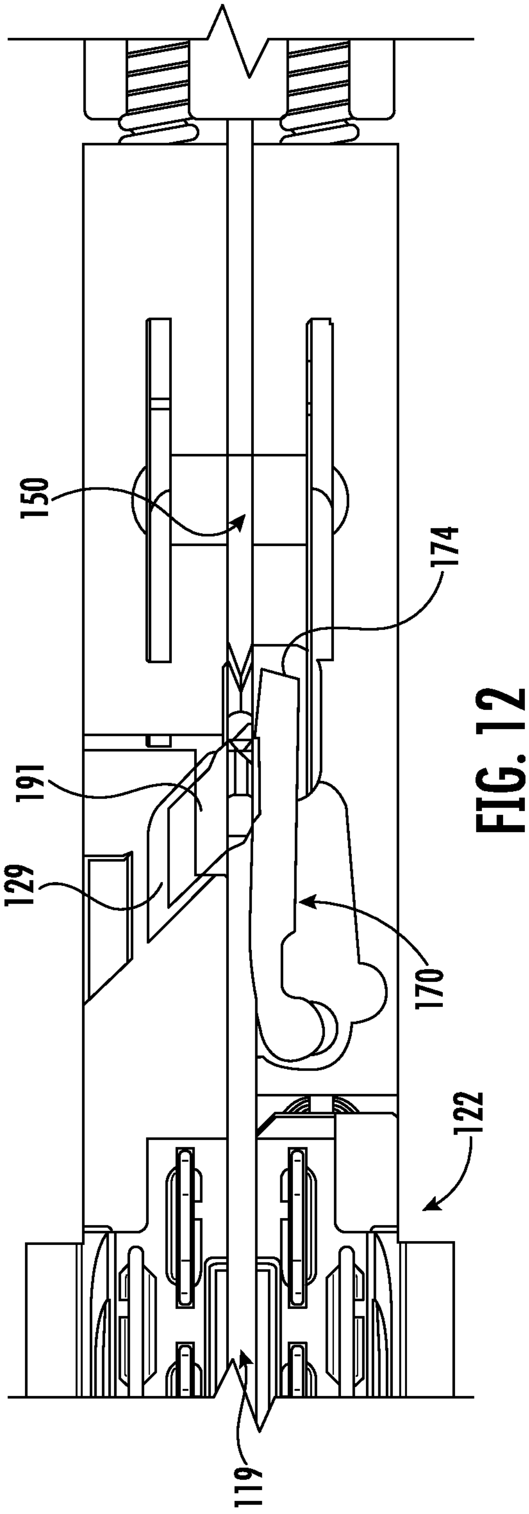
FIG. 12 depicts a partial perspective view of the stapler cartridge and instrument in the initial position after a fresh stapler cartridge has been installed.

Referring now to FIGS. 4-6, one embodiment of a stapler cartridge 122 will now be described. As shown, cartridge 122 comprises a housing 500 having a central channel 119 for receiving drive member 150 (shown in FIG. 12 and discussed below) and first and second staple receiving assemblies 502, 504 extending longitudinally on either side of central channel 119. Each staple receiving assembly 502, 504 comprises at least one linear row of staple pockets 127 for receiving staples 124. In some embodiments, staple assemblies 502, 504 comprise two or more substantially parallel, linear rows of staple pockets 127. Cartridge 122 may further include one or more openings 506 for cooperating with detents (not shown) in second jaw 112, and one or more lateral protrusions 508 extending from a distal portion of housing 500 for cooperating with associated recesses in jaw 112.

As best shown in FIG. 5, cartridge housing 500 defines a tissue contacting surface 510 that will contact tissue when jaws 111, 112 close around the tissue. Tissue contacting surface 510 may extend laterally across housing 500 from the outside portion of staple assembly 502 to the opposite, outside portion of staple assembly 504. Tissue contacting surface 510 includes first and second lateral portions 512, 514 that generally overlie staple assemblies 502, 504 and a central portion 516 that is recessed within housing 500 relative to lateral portions 512, 514. In a preferred embodiment, central portion 516 is recessed below a plane that is co-planar with the upper surfaces of projections 508 and/or the upper surfaces of jaw 112 (see FIG. 2). The term "upper" in this context means the surfaces on cartridge 122 or jaw 112 that face towards upper jaw 111. In certain embodiments, central portion 516 is preferably recessed by a distance large enough to increase the effective length of the tissue away from the line of dissection, while still having sufficient thickness in the material underlying central portion 516 to maintain the overall integrity of housing 500.

Central portion 516 of tissue contacting surface 510 creates a jog in the plane in which the tissue sits between jaws 111, 112 of the device, thereby increasing the length of tissue contacting surface 510 between the middle of central channel 119 and staple assemblies 502, 504. This jog causes tissue to fold or bend into central portion 516 as jaws 111, 112 close upon the tissue, thereby increasing the width of the tissue between the line of dissection and the staples.

As discussed in more detail below, drive member 150 includes a cutting element 128 (see FIG. 11) that passes through central channel 119 to dissect tissue. Simultaneously with the dissection of tissue, staples 124 are driven into the tissue on either side of the line of dissection. Accordingly, increasing the length of tissue contacting surface 510 between staple assemblies 502, 504 and the center of central channel 119 increases the width of the tissue cuff between the line of dissection and the stapled tissue, thereby minimizing deformation of the staples and fraying of tissue which results in a more optimal seal of the tissue.

In an exemplary embodiment, central portion 516 includes first and second lateral walls that extend from lateral portions 512, 514 in a direction substantially perpendicular to tissue contacting surface 510 along lateral portions 512, 514. Of course, it will be recognized that other configurations are possible. For example, the lateral walls of central portion 516 may be inclined such that they extend at a transverse, but non-perpendicular, angle to tissue contacting surface 510.

In certain embodiments, housing 500 may further comprise a raised edge 530 extending longitudinally between each of the staple assemblies 502, 504 and central channel 119 (see FIG. 6). This raised edge 530 further increases the length of tissue contacting surface 520 between staple assemblies 502, 504 and the middle of central channel 119 because it forces the tissue to fold or bend over raised edge 530 and then down into recessed central portion 516.

In an alternative embodiment, upper jaw 111 may include a "jog" in the tissue contacting surface in the lower surface of jaw (i.e., the surface facing staple cartridge 122). In this embodiment, jaw 111 may include a lower tissue contacting surface (not shown) that has a central recessed portion that recesses upward away from staple cartridge 122. This central recessed portion of jaw 111 may be included as an alternative to, or in addition to, the central recessed portion 516 of cartridge 122.

Figure 7A:
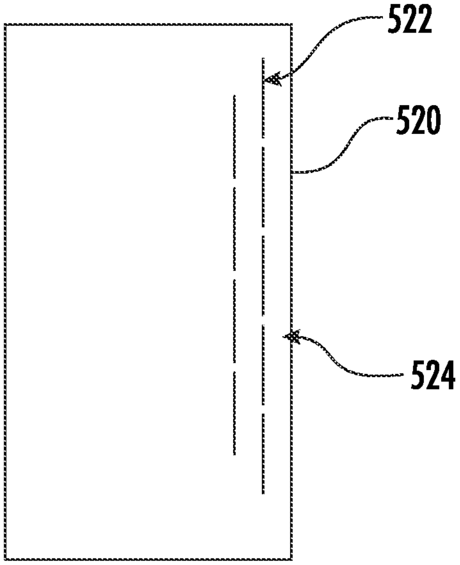
FIG. 7A (PRIOR ART)
FIG. 7A is a schematic illustration of a tissue cuff after dissection and stapling of tissue with a prior art surgical instrument.
Figure 7B:
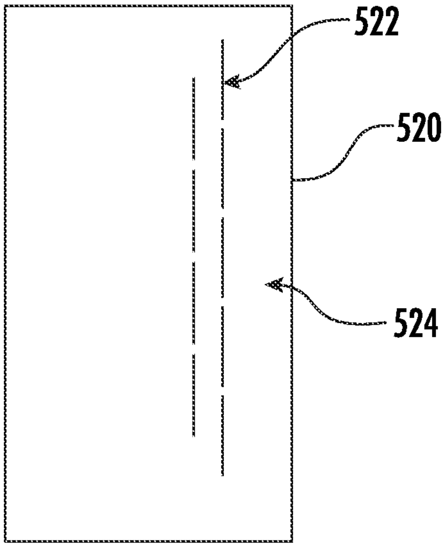
FIG. 7B is a schematic illustration of a tissue cuff after dissection and stapling of tissue with a surgical instrument disclosed herein.

FIGS. 7A and 7B illustrate the advantages of this embodiment. As shown in FIG. 7A, in a conventional stapler instrument (particularly a smaller stapler instrument having staples of less than 12 mm width), the line of tissue dissection 520 is very close to the line of staples 522, leaving a relatively small amount of tissue cuff 524 therebetween. With the staple cartridge shown in FIGS. 4-6, however, the line of dissection 520 is further away from the line of staples 522, leaving a substantially wider tissue cuff 524 (see FIG. 7B). This wider tissue cuff ensures that the stapled tissue is not frayed or otherwise damaged by cutting element 128.

Figure 8:
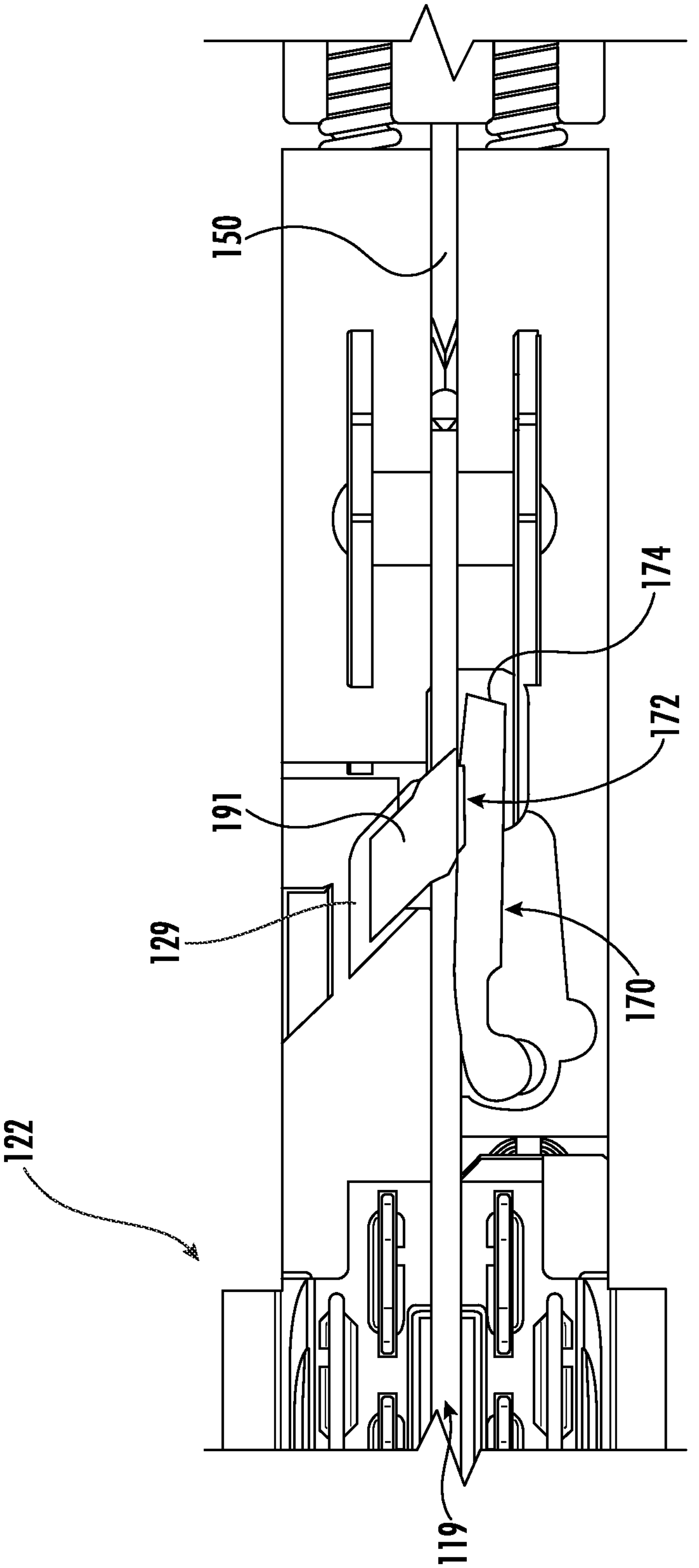
FIG. 8 depicts a partial top view of the end effector of a surgical stapling instrument including a lockout assembly having an unfired reload installed.

FIG. 8 shows a portion of an illustrative surgical instrument with an unfired stapler cartridge or reload installed, including portions of stapler cartridge 122, a locking member 170, and switch 191. When an unfired reload is installed, switch 191 is in a first home (or default) position. In a fresh, unfired reload, switch 191 is in contact with switch engaging portion 172 of locking member 170, keeping engagement portion 174 out of channel 119. When locking member 170 is in this disabled position, distal translation of drive member 150 is permitted, as locking member 170 will not obstruct movement of drive member 150 because engagement portion 174 is held out of alignment with channel 119.

Figure 9:
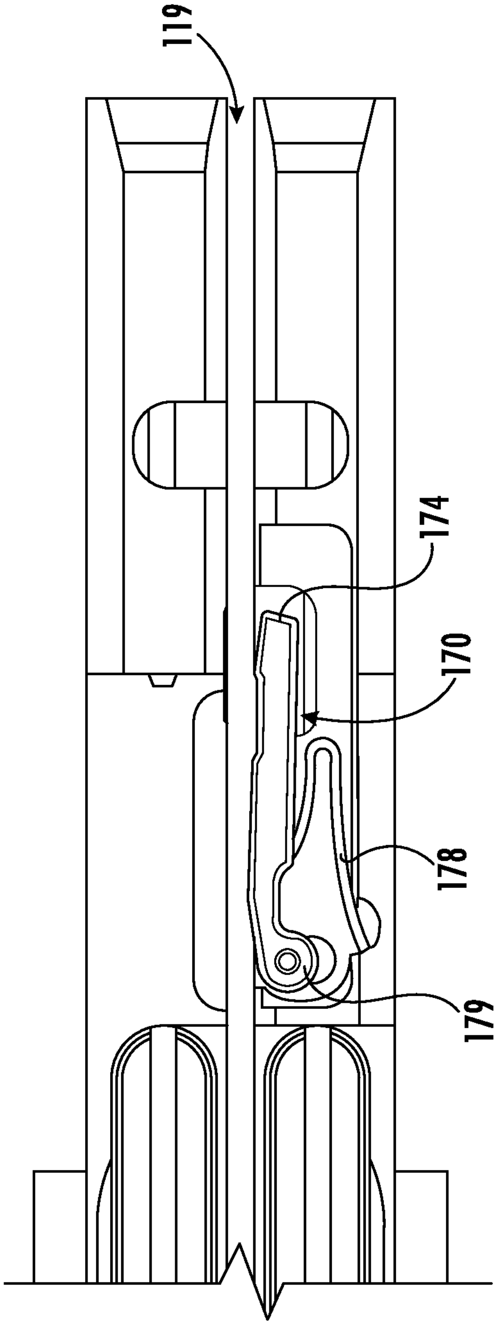
FIG. 9 depicts a top view of a lockout assembly in accordance with the embodiment of FIG. 8 in the unlocked position.
Figure 10:
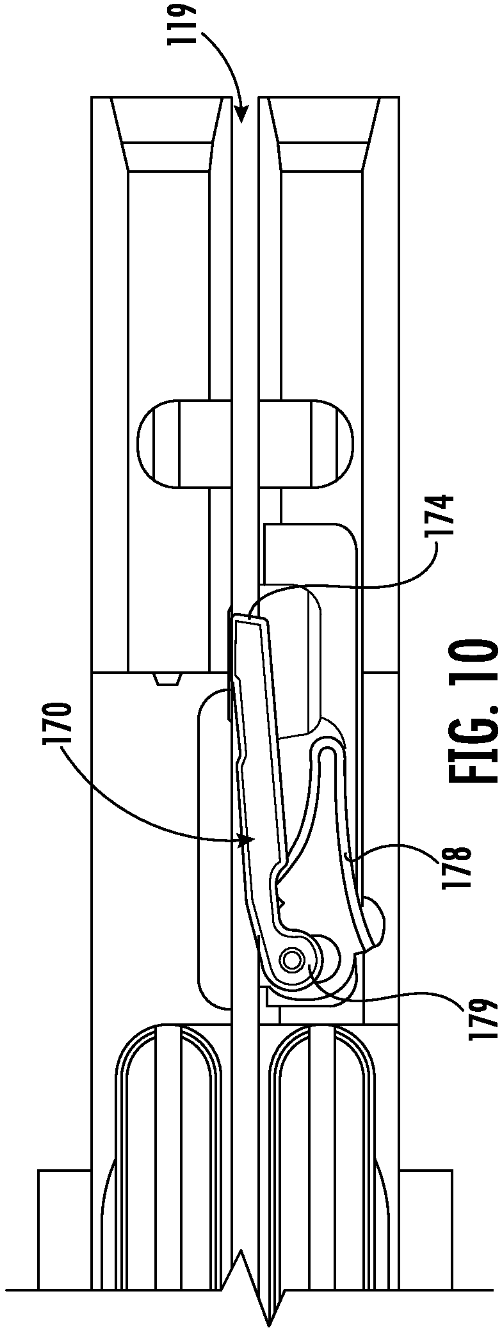
FIG. 10 depicts a top view of a lockout assembly in accordance with the embodiment of FIG. 8 in the locked position.

FIGS. 9 and 10 show a top view of a locking assembly including a locking member 170 in the unlocked or disabled position and the locked position, respectively with switch 191 not shown. Locking member 170 pivots about a pivot point 179 that is laterally offset from channel 119. Locking member 170 is configured to move in a direction substantially perpendicular to the longitudinal axis of the end effector. Spring 178 biases engagement portion 174 of locking member 170 into channel 119 to lock the instrument. In the unlocked position of FIG. 9, switch 191 (see FIG. 8) engages switch engaging portion 172 of locking member 170, overcoming the bias of spring 178 and holding engagement portion 174 out of channel 119, permitting distal movement of drive member 150. When switch 191 is no longer in contact with switch engaging portion 172 of locking member 170, spring 178 forces engagement portion 174 of locking member into channel 119 as seen in FIG. 10, where engagement portion 174 obstructs distal movement of drive member 150.

Figure 11:
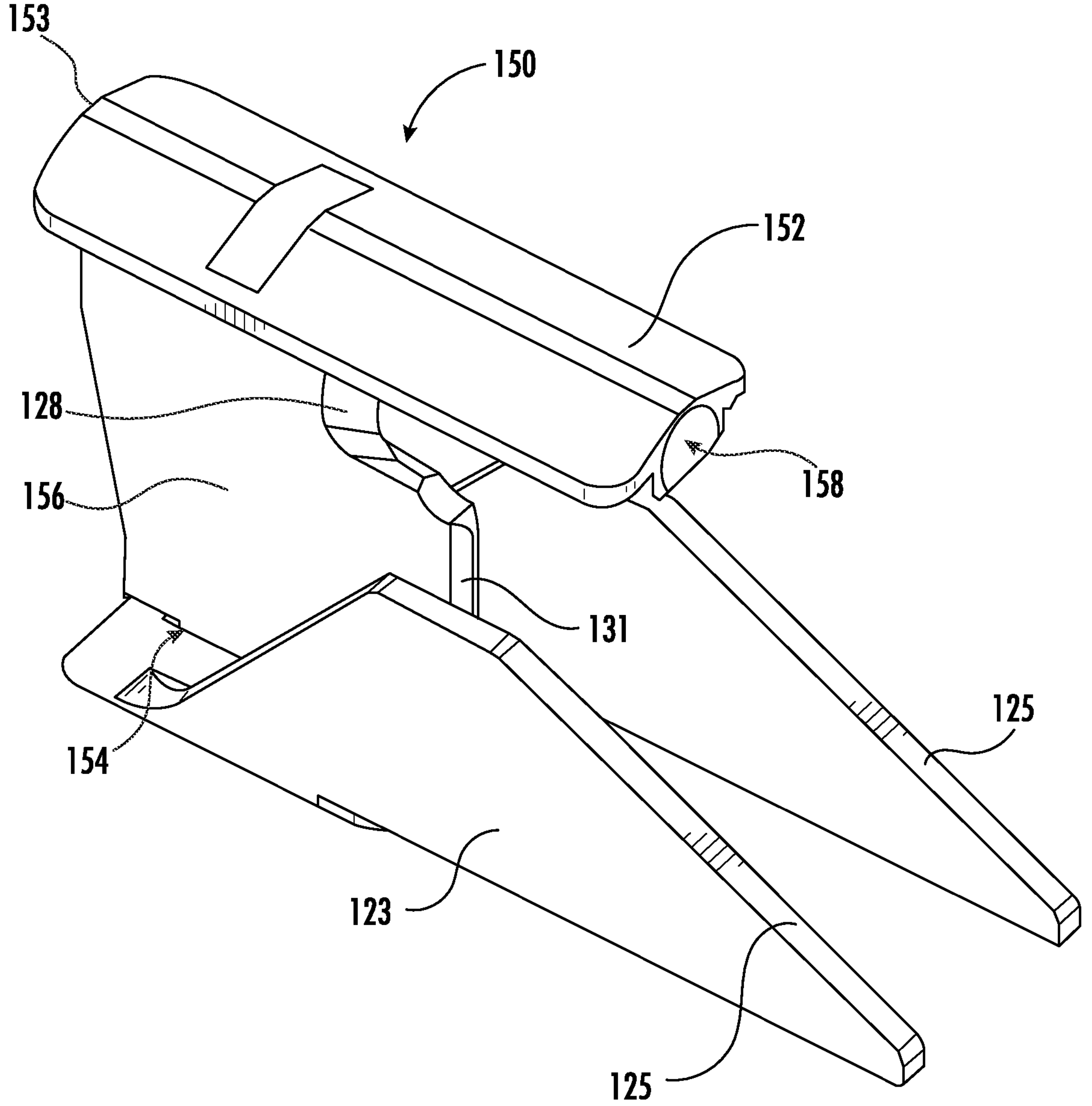
FIG. 11 is a perspective view of a drive member in accordance with the illustrative surgical instrument of FIG. 1.
Figure 13:
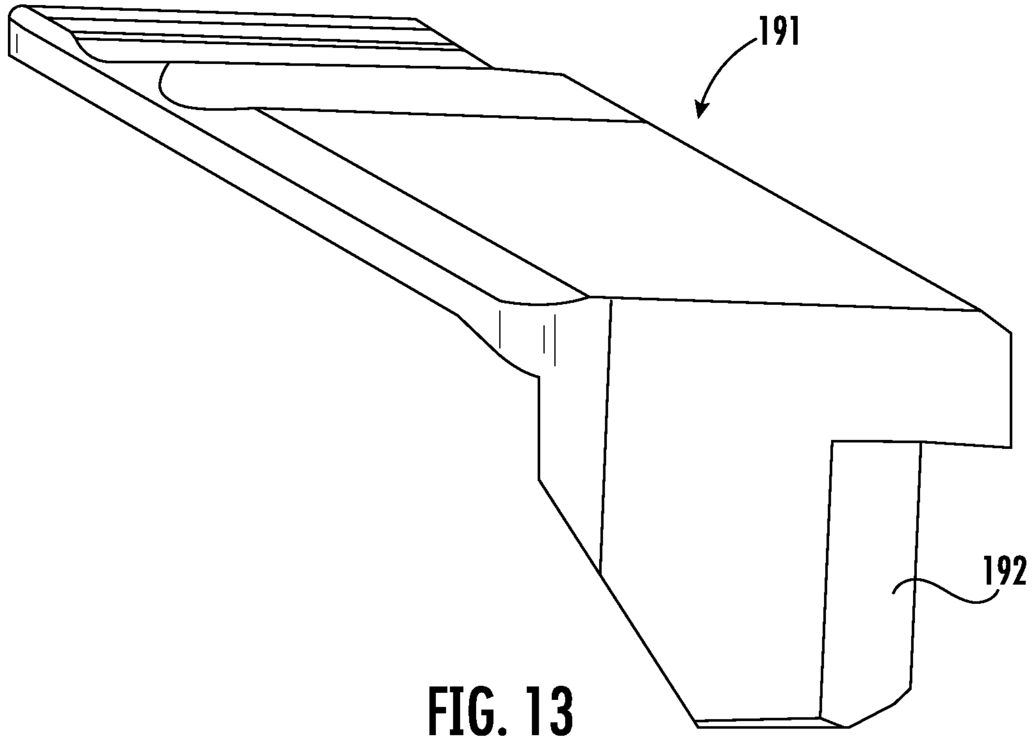
FIG. 13 is a perspective view of a switch in accordance with the illustrative surgical instrument of FIG. 1

Upon distal translation of drive member 150 during actuation of the instrument, a chamfered surface 131 formed on drive member 150 (as seen in FIG. 11) engages a chamfered surface 192 formed on switch 191 (as seen in FIG. 13). Switch 191 is then driven through a switch channel 129 in a direction substantially perpendicular to the longitudinal axis of end effector 110.

Figure 14B:
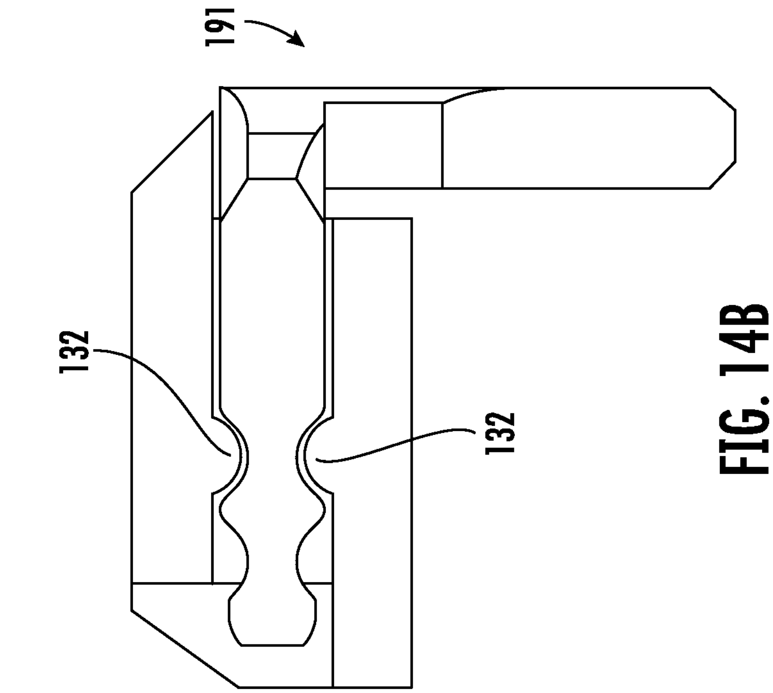
FIG. 14B depicts a partial side view of the switch of FIG. 13 in the second position after engagement with a drive member.
Figure 14A:
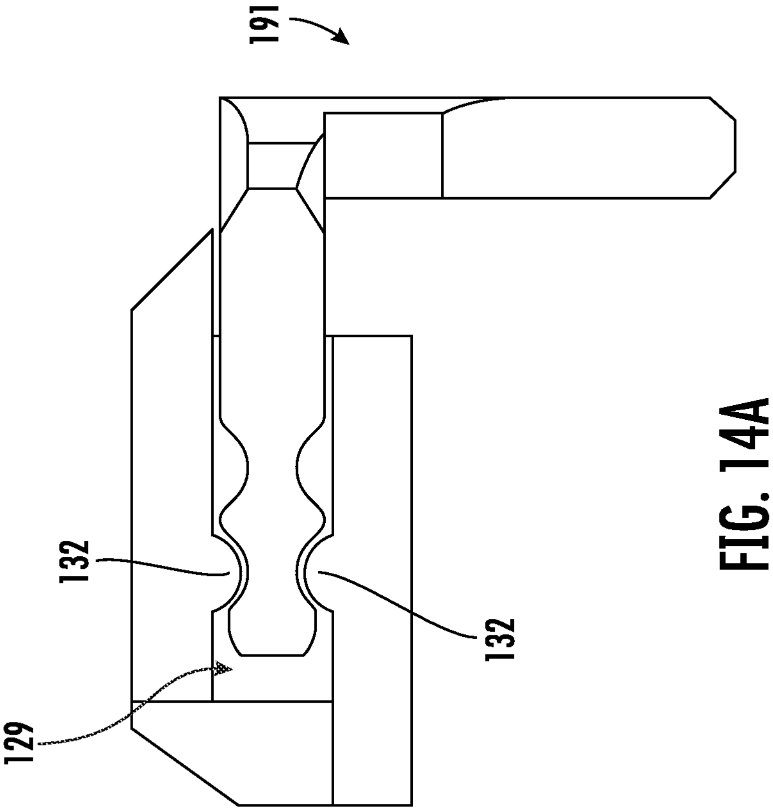
FIG. 14A depicts a partial side view of the switch of FIG. 13 in the first position prior to engagement with a drive member.

In FIG. 14A, switch 191 is shown in the initial position within switch channel 129 of tail 195 of cartridge 122. Switch channel 129 includes a series of detents 132 configured to provide mechanical resistance that must be overcome by drive member 150 in order to slide switch 191 from the initial position toward the second position, shown in FIG. 14B. This ensures that switch 191 will remain in the second position after the drive member 150 has passed through channel 119. In addition, it ensures that the lockout will not unintentionally activate as may happen if switch 191 freely slides in channel 129 (e.g., in the absence of detents 132). This also may provide a detectable resistance when switch 191 is translated past detents 132, as discussed in more detail below. In other embodiments, switch 191 may be secured by a friction fit within switch channel 129.

As best seen in previously described FIG. 8, while drive member 150 translates distally along the longitudinal axis defined by end effector 110, switch 191 moves laterally through channel 129 in a direction perpendicular to the axis. This allows switch 191 to be retained the within end effector 110 on a side that is opposite locking member 170, such that switch 191 and locking member 170 do not have to compete for space within end effector 110, allowing for maintenance of reduced instrument size.

Figure 15:
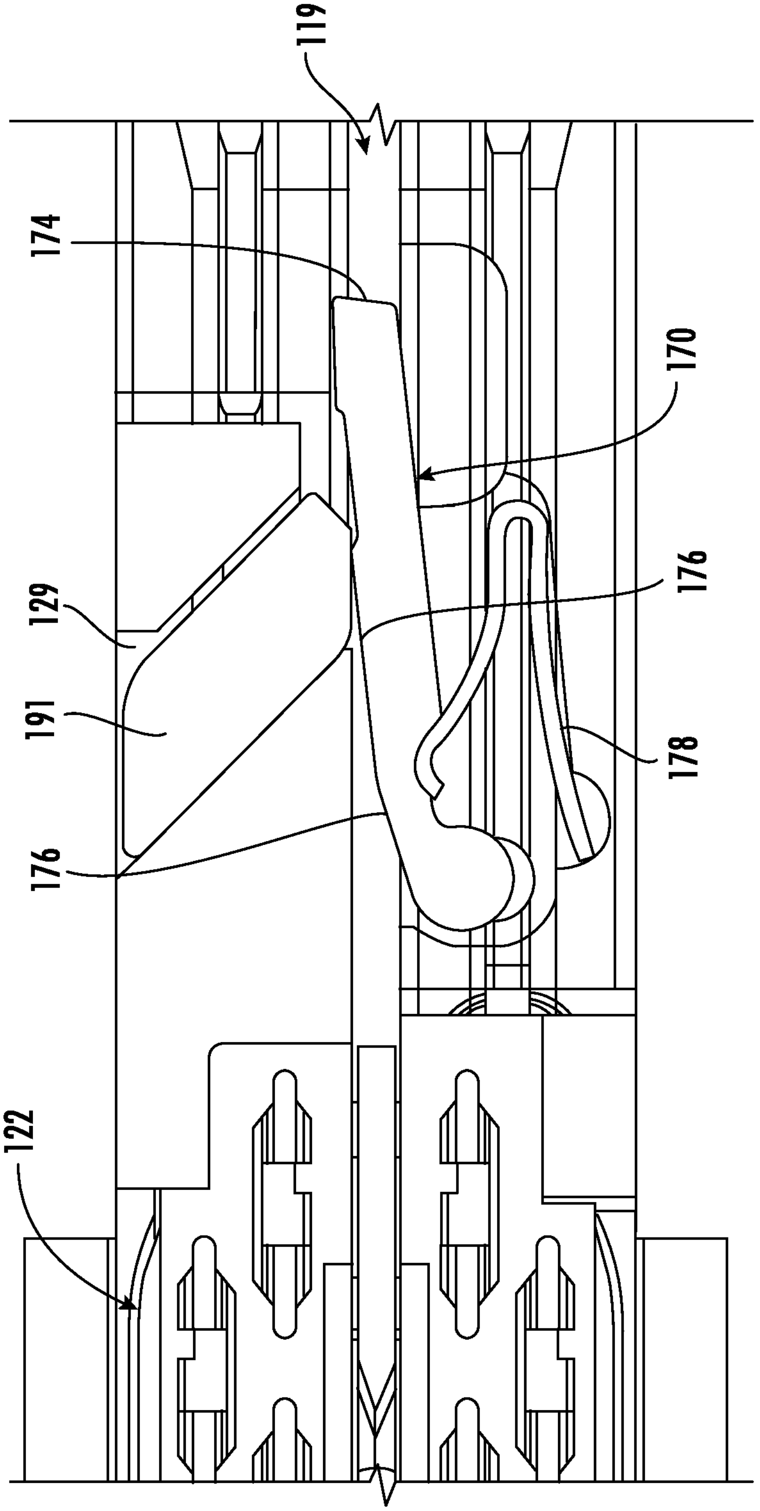
FIG. 15 is a partial cross-section view of the surgical instrument with the locking element in a locked position.
Figure 16:
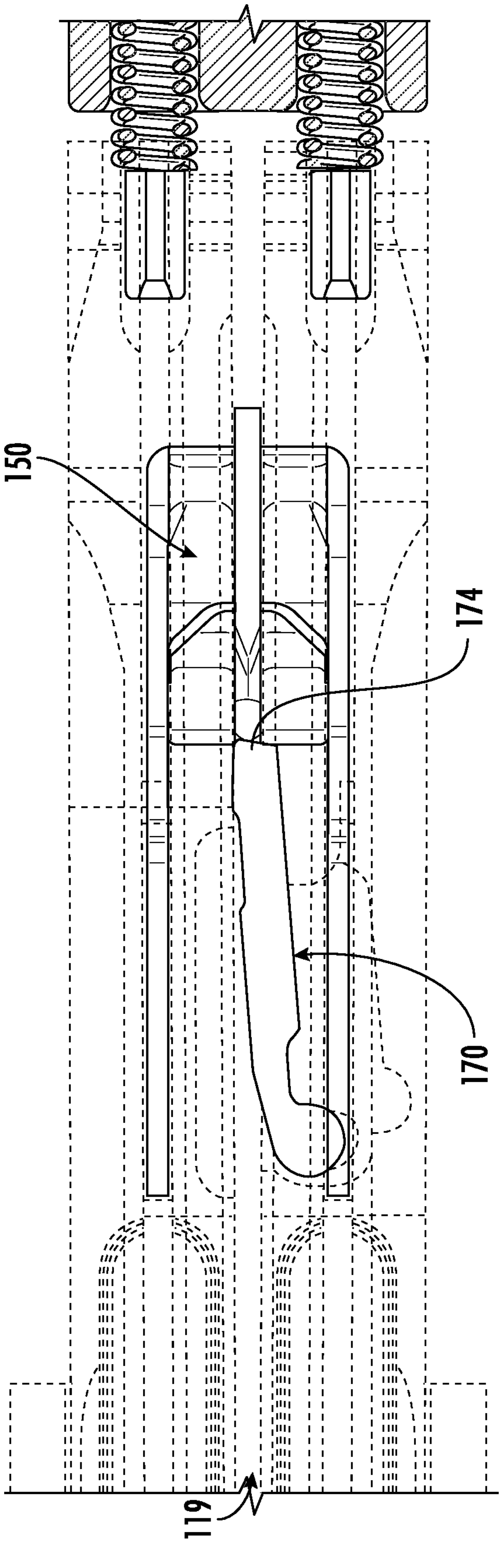
FIG. 16 is a partial side view of an end effector showing a drive member that has been fully retracted after firing, and a locking member that is enabled.

In FIG. 15, drive member 150 has translated distally, forcing switch 191 to the second position thereby enabling locking member 170, as spring 178 biases engagement portion 174 of locking member 170 into channel 119. Drive member 150 may continue to travel distally to drive staples into tissue and cut the stapled tissue. Upon retraction, drive member 150 engages a series of proximal ramped surfaces 176 on locking member 170, allowing drive member 150 to return to a position proximal of locking member 170. However, once drive member 150 is positioned proximally of locking member 170, if another attempt is made to actuate the instrument, drive member 150 will be obstructed by engagement portion 174 of locking member 150, preventing actuation of an unloaded instrument, as best seen in FIG. 16.

Figure 17:
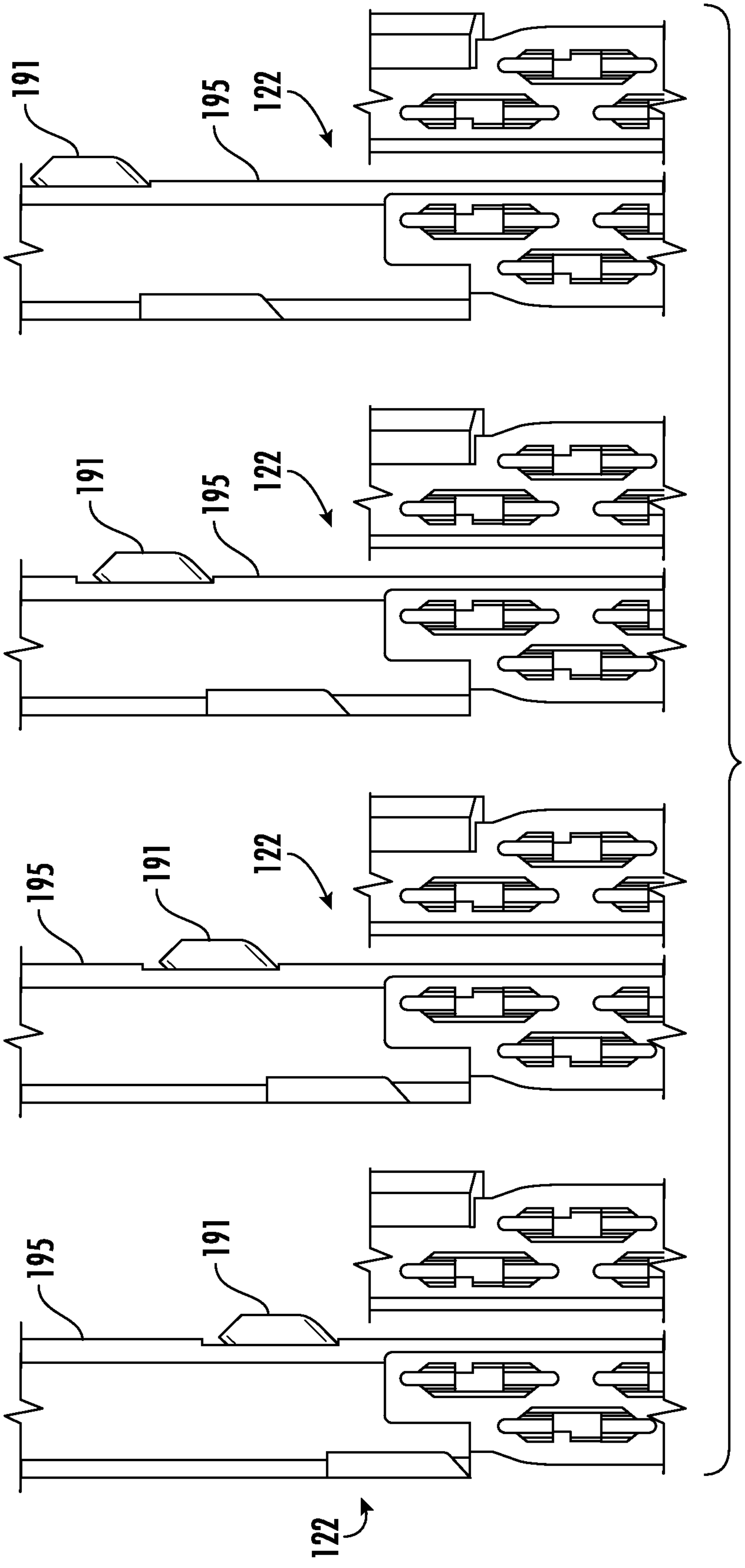
FIG. 17 is a partial top view of the proximal ends of a series of illustrative stapler cartridges having a switch in the initial position at various axial positions on the respective tail of each stapler cartridge.

FIG. 17 shows a series of illustrative cartridges having a switch 191 in the initial position at various axial positions on the respective tail 195 of each stapler cartridge 122. In embodiments, the axial position of switch 191 may function as a mechanism by which a control system, such as a robotically controlled surgical system, may identify the type of stapler cartridge installed. As drive member 150 translates through the end effector, it will encounter the switch at a distinct axial position for a given type of stapler cartridge. When the drive member encounters the switch, the drive member will encounter a detectable amount of resistance. In embodiments, a robotic surgical system may be configured to detect the position along a firing stroke at which the chamfered surface 131 formed on drive member 150 engages switch 191 via detection of a torque spike, allowing the system to determine the type of stapler cartridge installed. This will allow a control unit, operatively coupled with the actuation mechanism, to determine the correct amount of forces to apply to the drive member depending upon the features of the detected type of stapler cartridge, including but not limited to, the number of staples contained therein, the size of the staples contained therein, and the geometry of the staples contained therein. An exemplary surgical stapler including a surgical system including a control unit operatively coupled to the actuation mechanism is described for example in International Application No. PCT/US2017050747, the disclosure of which is hereby incorporated by reference in its entirety.

Figure 18:
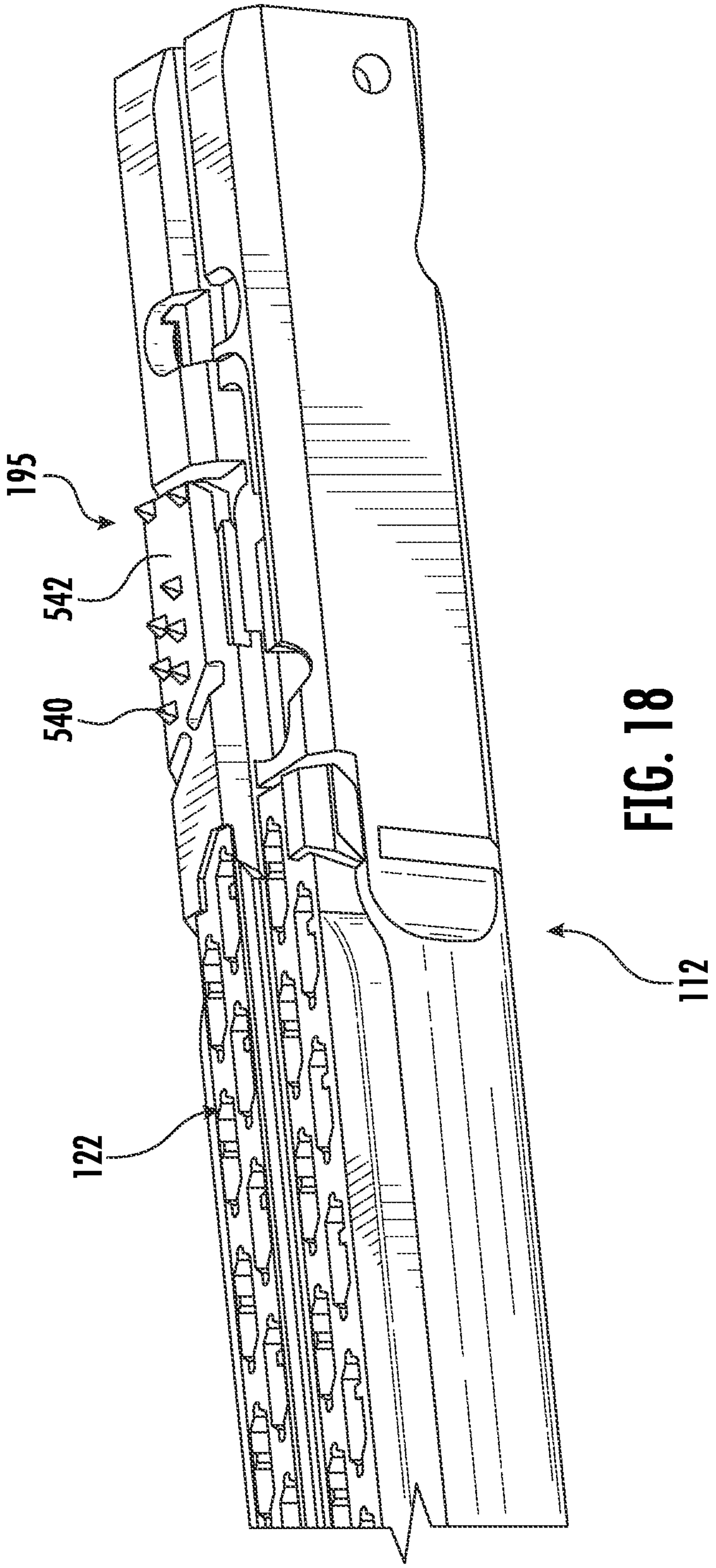
FIG. 18 is a perspective view of one portion of a stapler cartridge and surgical instrument.

Referring now to FIG. 18, in certain embodiments, staple cartridge 122 may include one or more protrusions 540, bumps or other surface features on an upper surface 542 of tail portion 195. Protrusions 540 preferably comprise any suitable deformable material that will function to inhibit vertical movement of tail portion 195 of cartridge 122 relative to the upper jaw 111. Alternatively, protrusions 540 may be configured to interlock with each other, or they may be configured to create friction with upper jaw 111 in order to inhibit the vertical movement of tail portion 540. This stabilizes the proximal portion of stable cartridge 122 relative to the jaws 111, 112 during actuation of the instrument and/or during reload detection.

In certain embodiments, protrusions 540 extend from upper surface 542 of tail portion 195 to at least the lower surface of jaw 111 when the first and second jaws 111, 112 are in the closed positions. In other embodiments, protrusions 540 may be sized with a larger height than the distance between jaw 11 and tail portion 195 in the closed configuration to create interference therebetween. In some embodiments, protrusions 540 are configured to deform to this height to take up any clearance therebetween.

Protrusions 540 may have any suitable shape that performs the function of taking up clearance between the jaw 111 and proximal tail 195, such as pyramidal, conical, cylindrical, rectangular, square or the like. In an exemplary embodiment, protrusions 540 have a substantially pyramidal shape with a base extending from proximal tail 195 to a tip that may be pointed or flat. This shape allows for vertical deformation of protrusions 540 as jaw 111 is closed onto tail 195.

In an alternative embodiment, protrusions 540 may be formed on upper jaw 111. In this embodiment, protrusions 540 would be formed on the lower surface of upper jaw 111 so as to perform the same function of taking up any clearance between jaw 111 and proximal tail 195 of the staple cartridge. In certain embodiments, protrusions 540 may be formed on both jaw 111 and proximal tail 195.

In another alternative embodiment, protrusions 540 may be formed on the lower surface (not shown) of proximal tail 195. In this embodiment, protrusions 540 serve to take up any space or clearance between the lower surface of proximal tail 195 and lower jaw 112 and/or other components of end effector 110 that may reside beneath proximal tail 195. Similar to the previous embodiments, protrusions 540 inhibit vertical movement of proximal tail 195 relative to lower jaw 112 and/or end effector 110. In yet another embodiment, protrusions 540 may be formed on both the upper and lower surfaces of proximal tail 195. In yet another embodiment, protrusions 540 may be formed on lower jaw 112, lower surface of proximal tail 195 and/or other components of end effector 110.

As drive member 150 is translated distally through channel 119, chamfered surface 131 formed on drive member 150 (as seen in FIG. 11) engages chamfered surface 192 formed on switch 191. The distal force applied against chamfered surface 192 applies a force to the switch 191 in the longitudinal and lateral directions. In addition, drive member 150 creates a torque against switch 191 and tail portion 195 that applies a force to tail portion 195 in both the lateral direction and in the vertical direction (i.e., towards upper jaw 111). Forces applied in the lateral direction are generally resisted by the side walls of jaw 112. Forces applied in the vertical direction are generally resisted by upper jaw 111 when jaws are in the closed position. However, this vertical force can cause tail portion 195 to move upwards toward jaw 111 if there is any space between jaw 111 and upper surface 542 of tail portion 195, thereby creating instability in staple cartridge 122 during actuation. Protrusions 540 stabilize tail portion 195 of cartridge 122 by taking up any clearance and deforming against jaw 111 to the closed height between jaw 111 and cartridge 122.

Figure 19:
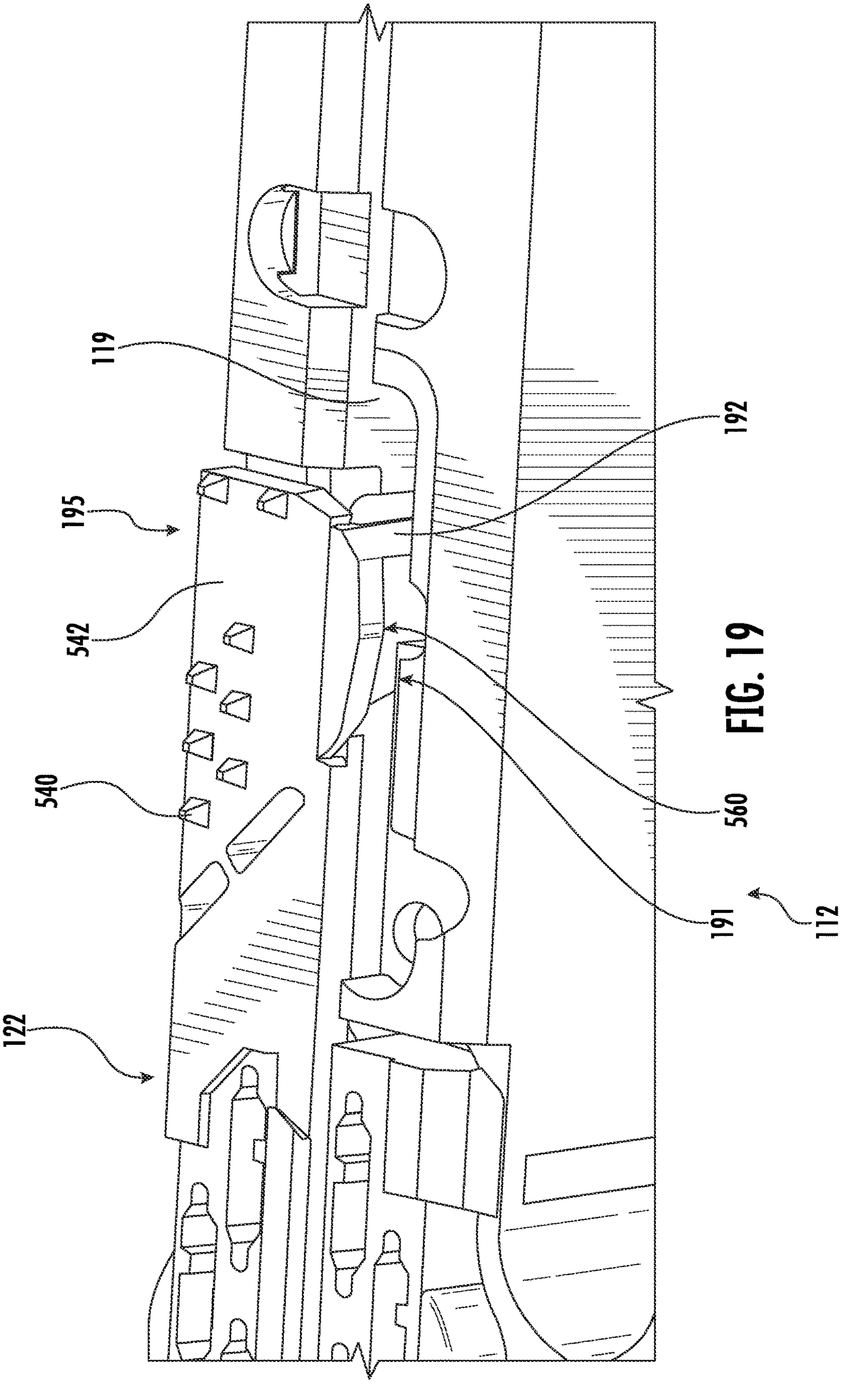
FIG. 19 is a close-up view of the stapler cartridge and surgical instrument of FIG. 18.
Figure 20:
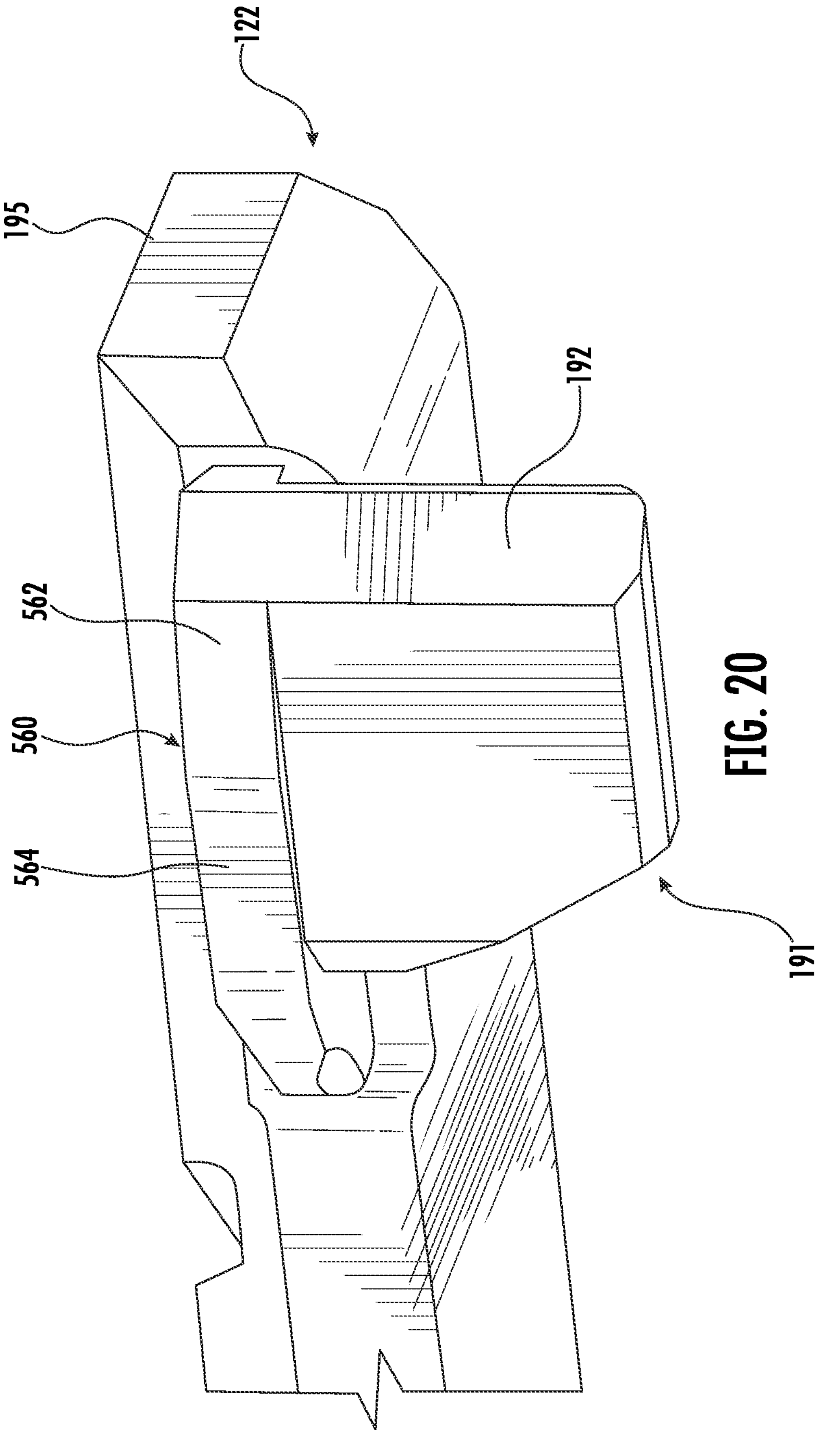
FIG. 20 is a perspective view of a switch of the stapler cartridge of FIG. 18.

Referring now to FIGS. 19 and 20, an alternative embodiment of switch 191 will now be described. As shown, switch 191 includes a chamfered surface 192 for contacting surface 131 of drive member 150, as described above. In addition, switch 191 comprises a lobe 560 that extends laterally outward from switch 191 into channel 119. Lobe 560 preferably comprises a proximal inclined surface 562 and a distal inclined surface 564. Alternatively, distal surface 564 may be substantially parallel with the longitudinal axis of staple cartridge 122. Proximal inclined surface 562 extends from chamfered surface 192 in a distal direction. Proximal inclined surface 562 preferably extends transversely into channel 119 at an angle that is smaller relative to the longitudinal axis than the angle of chamfered surface 192. In a preferred embodiment, inclined surface 562 extends further distally than laterally (i.e., an angle of less than 45 degrees with the longitudinal axis, preferably less than 30 degrees).

Chamfered surface 192 and proximal inclined surface 562 together make a combined contact surface for contacting surface 131 of drive member 150. In particular, inclined surface 562 extends the time and distance of contact between drive member 150 and switch 191 as drive member 150 translates through channel 119 (referred to as "switch stroke"). In embodiments, chamfered surface 192 and proximal inclined surface 562 preferably extend in the longitudinal direction a combined distance that is equal to or greater than the thickness of central portion 156 of drive member 150.

Increasing the overall stroke of switch 191 mitigates issues that may be caused by insufficient switch stroke. For example, an increased switch stroke ensures that switch 191 will move laterally out of the path of drive member 150 during distal translation of drive member 150. Once switch 191 has moved a sufficient lateral distance, it is retained within slot 129 of proximal tail 195 so that it cannot move back into channel 119 after drive member 150 has moved past the switch 191. Therefore, moving switch 191 laterally into slot 129 ensures that drive member 150 will not get stuck on switch 191 as it is retracted proximally. If drive member 150 were to get stuck during the proximal retraction, the jaws of the instrument would not completely open and the instrument could become stuck to the tissue, resulting in potential tissue damage and unnecessary delays in the procedure.

In certain embodiments, 191 switch may be configured to provide a detectable resistance upon engagement of drive member 150 with surfaces 192, 562 in order to, for example, provide input for a reload detection mechanism that can detect: whether a stapler cartridge is mounted to the surgical instrument; whether the mounted stapler cartridge is unfired (or fresh) or has already been fired; and/or the type of the mounted stapler cartridge mounted to the end effector to ensure that the mounted stapler cartridge has a suitable staple length for the tissue to be stapled, based on the detectable resistance. Increasing the switch stroke with inclined surface 562 also ensures that this detection mechanism is more reliable.

Of course, other configurations are possible. For example, chamfered surface 192 may be extended further into channel 119 to increase the switch stroke (e.g., rather than providing a lobe 560 with a second inclined surface 562). In this embodiment, chamfered surface 192 may have a smaller angle with the longitudinal axis of staple cartridge 122 than is presently shown in the figures. Chamfered surface 192 may, for example, extend at an angle less than 45 degrees, or less than 30 degrees, with the longitudinal axis. Thus, chamfered surface 192 would extend further in the distal direction to increase the time and distance of its contact with drive member 150 as drive member 150 is translated through channel 119.

In yet another embodiment, contact surface 131 of drive member 150 may be extended in the longitudinal direction to increase the switch stroke of drive member 150 and switch 192. In this embodiment, contact surface 131 may include an additional inclined surface, or it may be extended further at a suitable angle to allow for an increased amount of contact between switch 192 and drive member 150 as drive member 150 translates through channel 119.

Figure 21:
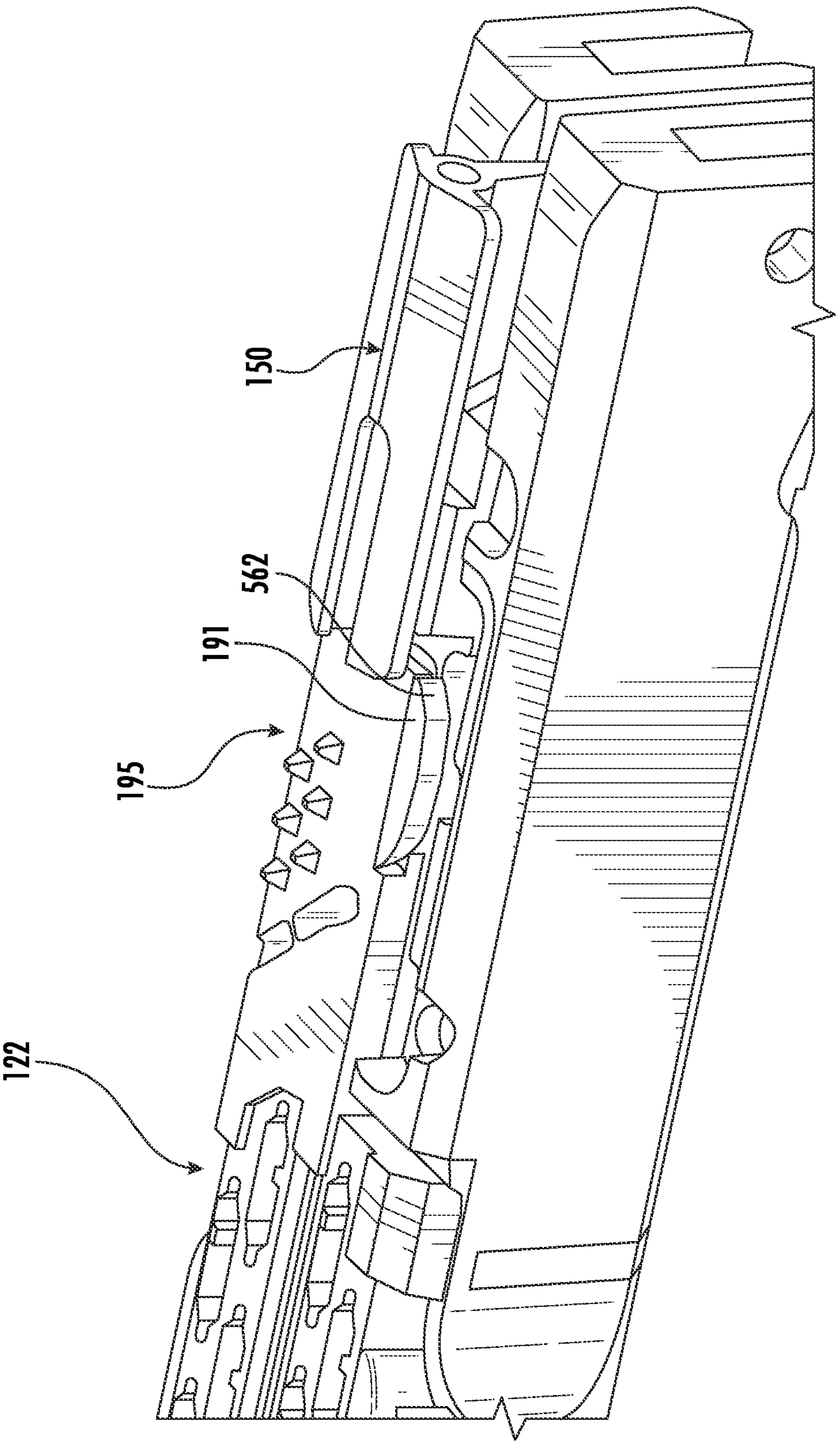
FIG. 21 is a perspective view illustrating a drive member of the surgical instrument positioned proximal of the switch of FIG. 20.
Figure 22:
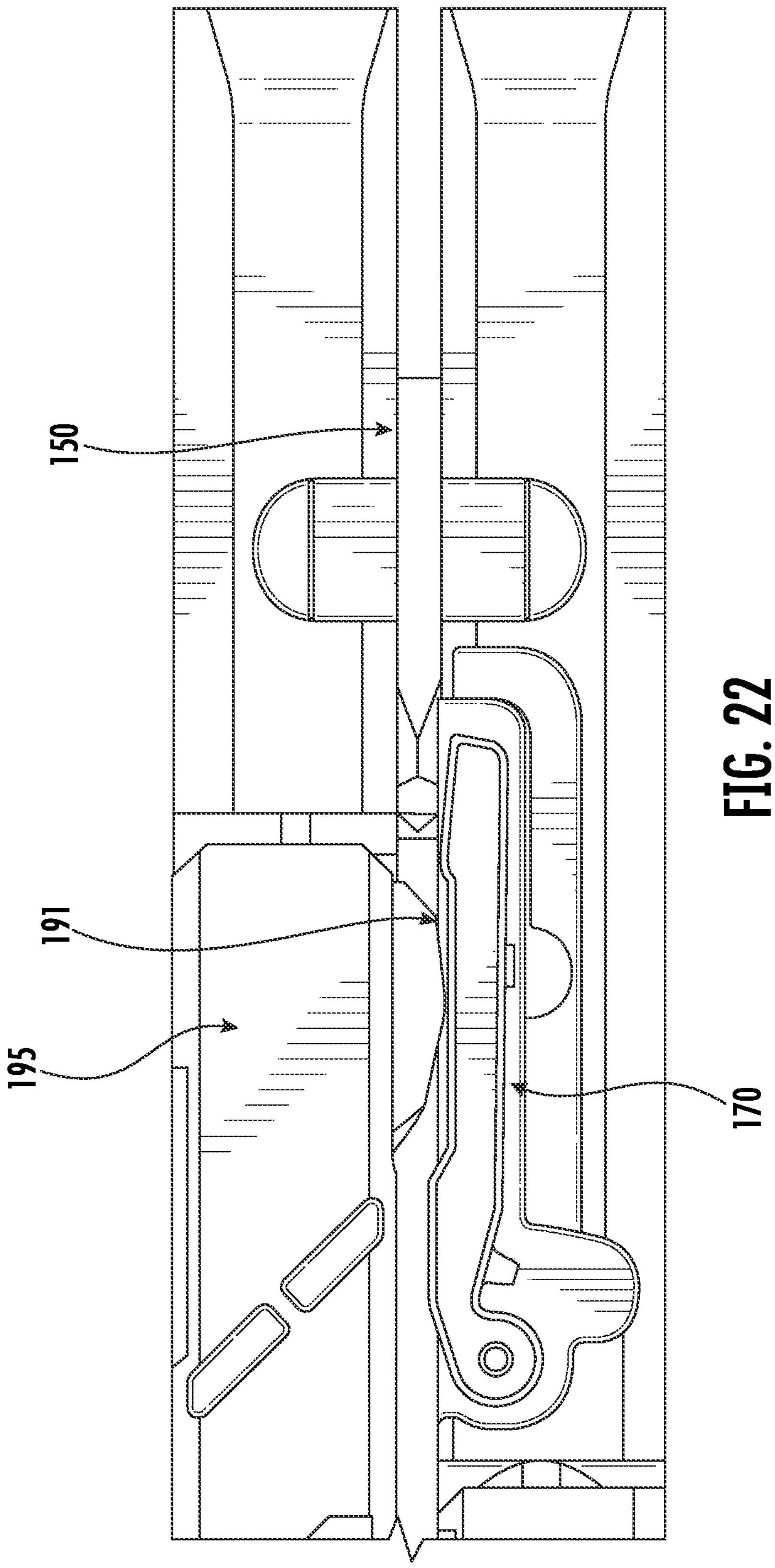
FIG. 22 is a partial cross-sectional view of the surgical instrument, illustrating a locking element in an unlocked position.
Figure 23:
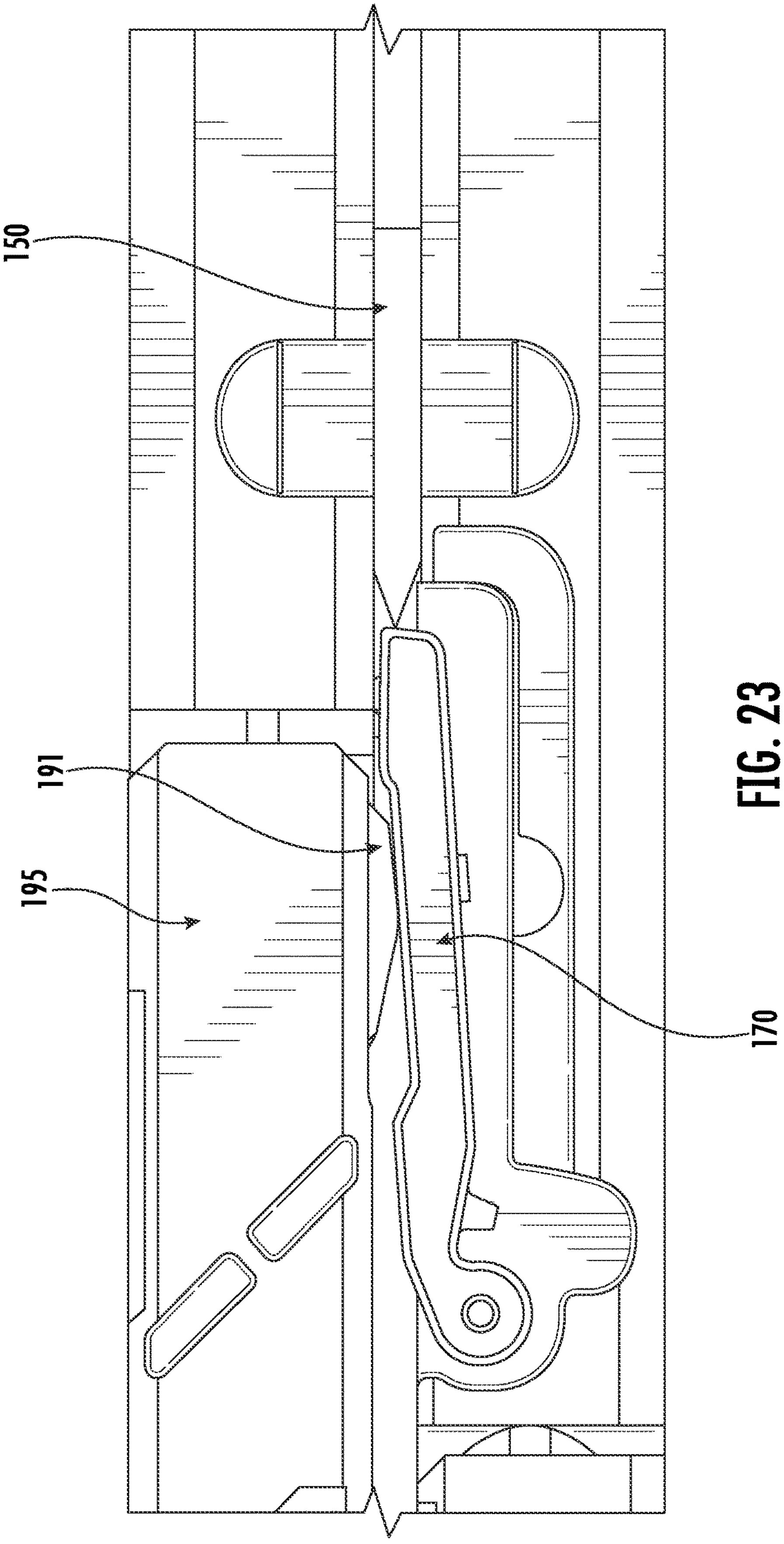
FIG. 23 is a side view of an end effector showing a drive member that has been fully retracted after firing, and a locking member that is enabled.

FIGS. 21-23 illustrate operation of drive member 150, locking member 170 and switch 191. As shown, when a new staple cartridge 122 is mounted to jaw 112, drive member 150 is disposed proximally to both locking member 170 and switch 191. Locking member 170 is in the enabled position that allows drive member 150 to translate distally through channel 119. Locking member 170 is biased towards the disabled position, but is held in place by switch 191. As drive member 150 translates distally, contact surface 131 engages chamfered surface 192 of switch 191 to move switch 191 laterally into slot 129 of proximal tail 195, as discussed above. Typically, this contact is sufficient to move switch 191 into slot, wherein it remains in place via detents 132, as described above.

In certain instances, however, a longer switch stroke may be required to completely move switch 191 into slot 129. Thus, as drive member passes chamfered surface 192, contact surface 131 then engages with proximal inclined surface 562 and continues to engage with switch 191 to provide more lateral force to drive switch 191 into slot 129. Once switch 191 has been driven into slot 129, locking member 170 pivots into the enabled position shown in FIG. 23. At this point, drive member 150 may retract proximally as discussed above. However, drive member 150 is unable to translate distally again until locking member 170 is moved back into the enabled position by switch 191.

Figure 24:
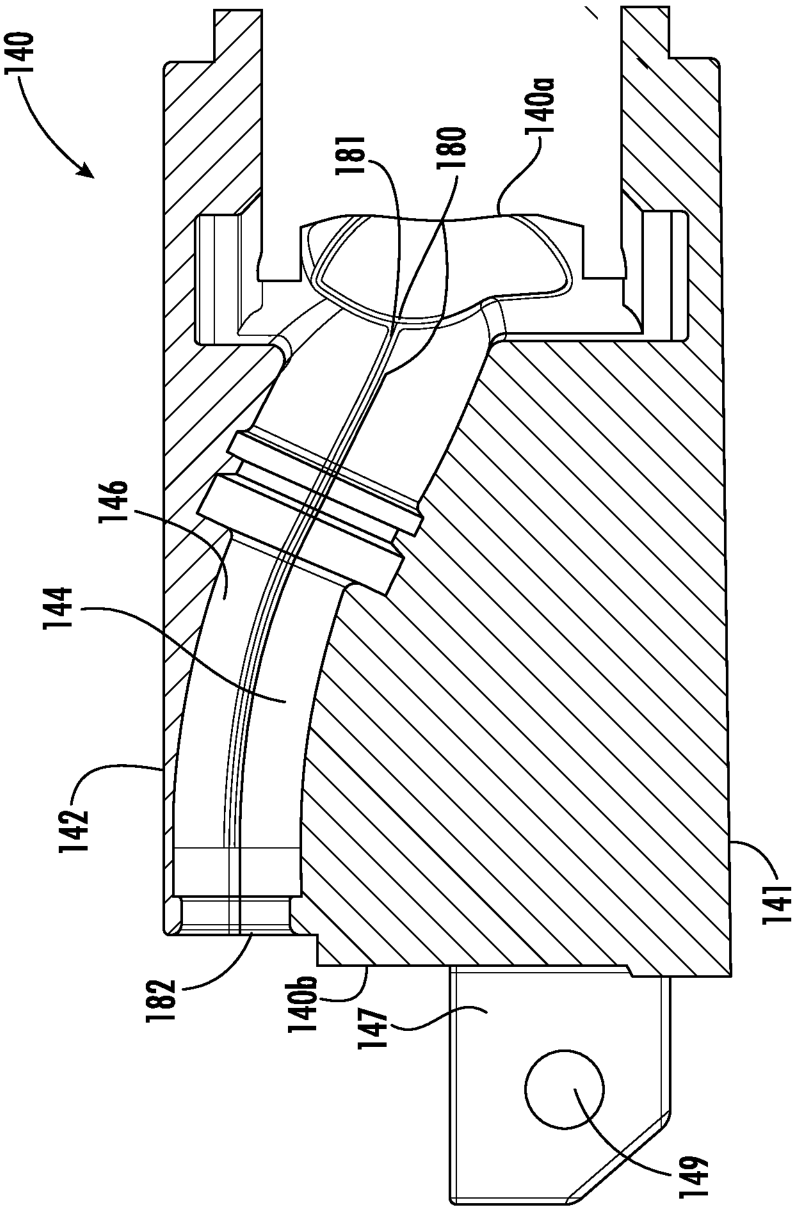
FIG. 24 is a cross-sectional side of a two-part clevis of the surgical instrument of FIG. 1.

Referring now to FIG. 24, jaws 111, 112 are attached to surgical instrument 100 via clevis 140. In certain embodiments, clevis 140 includes a proximal surface 140*a* and a distal surface 140*b*. Clevis 140 further includes upper clevis portion 142 and lower clevis portion 141 that cooperate when assembled to form protrusion 145 configured to engage tabs 113 (see FIG. 27A) of jaw 111 to securely mount jaw 111 in a fixed position on instrument 100. Lower clevis portion 141 includes a pair of distally extending arms 147 for supporting movable jaw 112. Arms 147 include opening 149 for receiving a pivot pin (not shown) defining a pivot axis around which jaw 112 pivots as described in more detail below.

Figure 25:
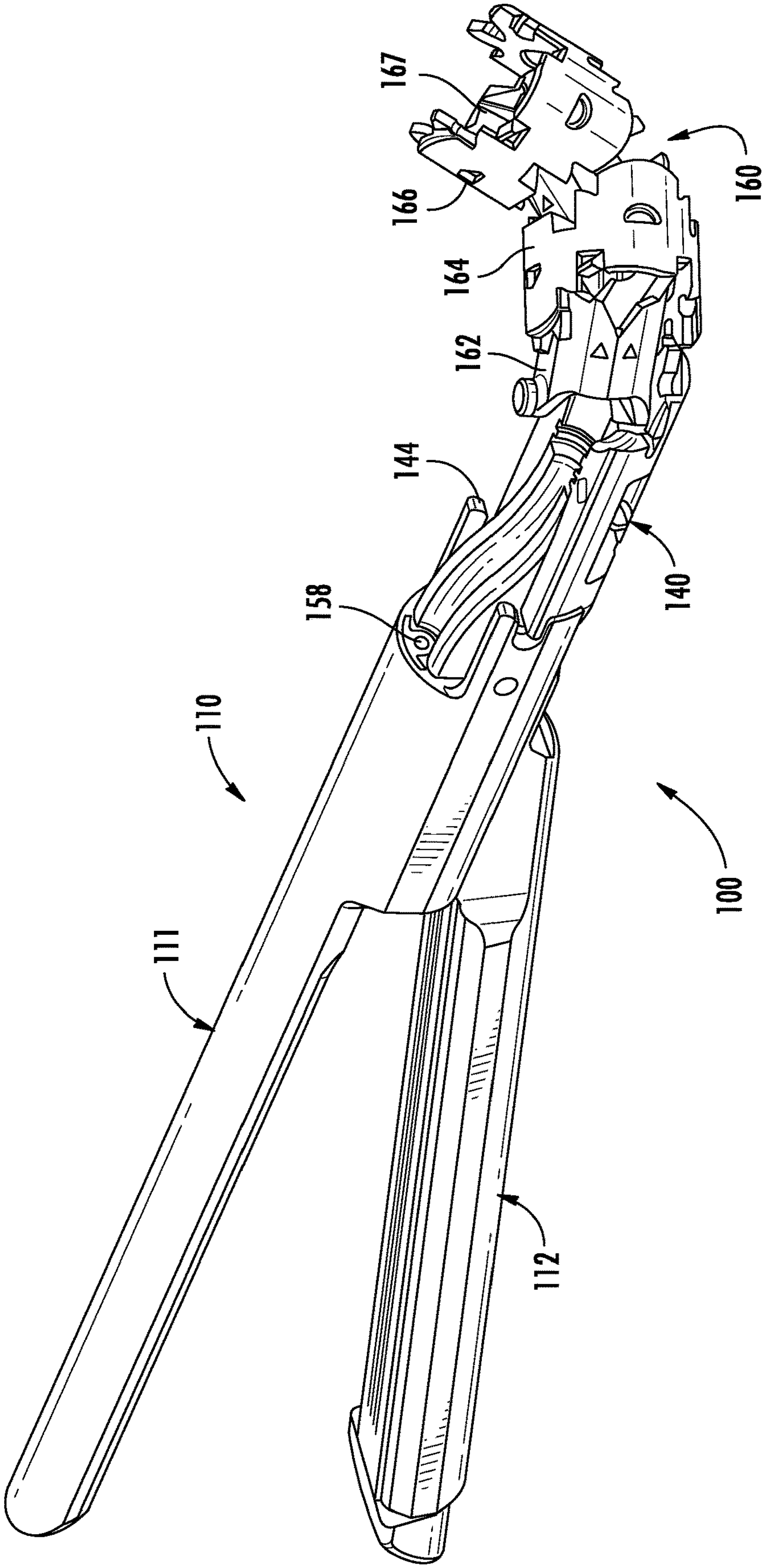
FIG. 25 is a perspective view of the end portion of an illustrative surgical instrument with parts removed.

Lower clevis portion 141 also includes ramped groove 144 configured to guide a portion of an actuation coil 120 (see FIG. 26A) emerging from wrist 160 (see FIG. 25). Upper clevis portion 142 includes a complementary shaped ramped groove 146 that cooperates with ramped groove 144 of lower clevis portion 141 to form an enclosed channel 180 that guides coil 120 as it jogs upwards from wrist 160 towards distal surface 157 of upper shoe 152 of drive member 150. In embodiments, channel 180 may include a first end 181 at a central portion of proximal surface 140*a* and a second end 182 at a peripheral portion of distal surface 140*b*. In embodiments, enclosed channel 180 may be substantially "S" shaped. Although shown as a two-part clevis, it should be understood that the clevis may be a unitary structure formed, for example, by molding, machining, 3-D printing, or the like.

End effector 110 may be articulated in multiple directions by an articulation mechanism. In embodiments, the articulation mechanism may be a wrist 160 as shown, although other articulation mechanisms are contemplated. As seen in FIG. 25, wrist 160 includes a plurality of articulation joints 162, 164, 166, etc. that define a bore 167 through which an actuation mechanism (in embodiments, coil 120 and drive cable 171, see FIG. 19A) may pass. Upon exiting articulation wrist 160, coil 120 enters and passes through channel 180 of clevis 140 (see FIG. 24), ultimately engaging proximal surface 153 (FIG. 11) of upper shoe 152 of drive member 150. Other articulation mechanisms within the purview of those skilled in the art may substitute for wrist 160. One suitable articulation mechanism is described for example in U.S. Publication No. 2015/0250530, the disclosure of which is hereby incorporated by reference in its entirety.

Upon actuation of the surgical instrument, drive member 150 is advanced distally through end effector 110 to move jaws 111, 112 from the open position to the closed position, after which shuttle 123 and knife 128 are advanced distally through cartridge 122 to staple and cut tissue grasped between jaws 111, 112. Drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through cartridge 122 and upper fixed jaw 111 and lower jaw 112 when the surgical stapling instrument is fired (e.g., actuated).

As seen in FIG. 11, drive member 150 may include an upper protrusion or shoe 152, a lower protrusion or shoe 154, and a central portion 156 connecting upper and lower shoes 152, 154. Upper shoe 152 of drive member 150 is substantially aligned with and translates through channel 118 in fixed jaw 111, while lower shoe 154 of drive member 150 is substantially aligned with and translates through channel 119 and below jaw 112. Bore 158 is formed through upper shoe 152 to receive a drive cable 171 as will be described in more detail below. Proximal surface 153 of upper shoe 152 is configured to be engaged by a coil 120 of an actuation assembly such that coil 120 may apply force to upper shoe 152 to advance drive member 150 distally, i.e., in the direction of arrow "A" in FIG. 26B. A knife 128 may be formed on drive member 150 along the distal edge between upper shoe 152 and central portion 156. In embodiments, inclined distal portions 125 may be formed on either side of drive member 150.

Figure 26A:
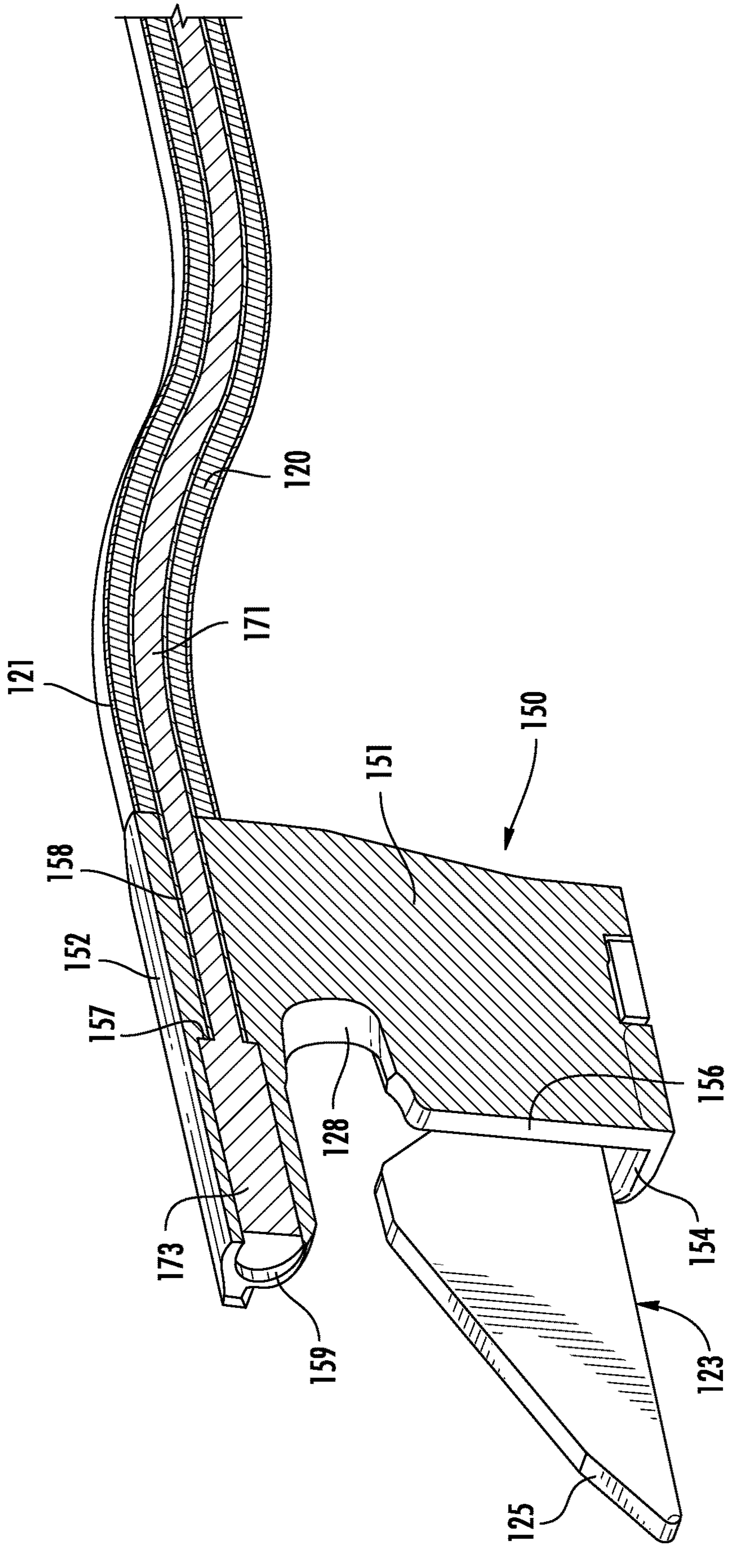
FIG. 26A is a cross-sectional perspective view of the actuation mechanism for a drive member in accordance with the surgical instrument of FIG. 1.
Figure 26B:
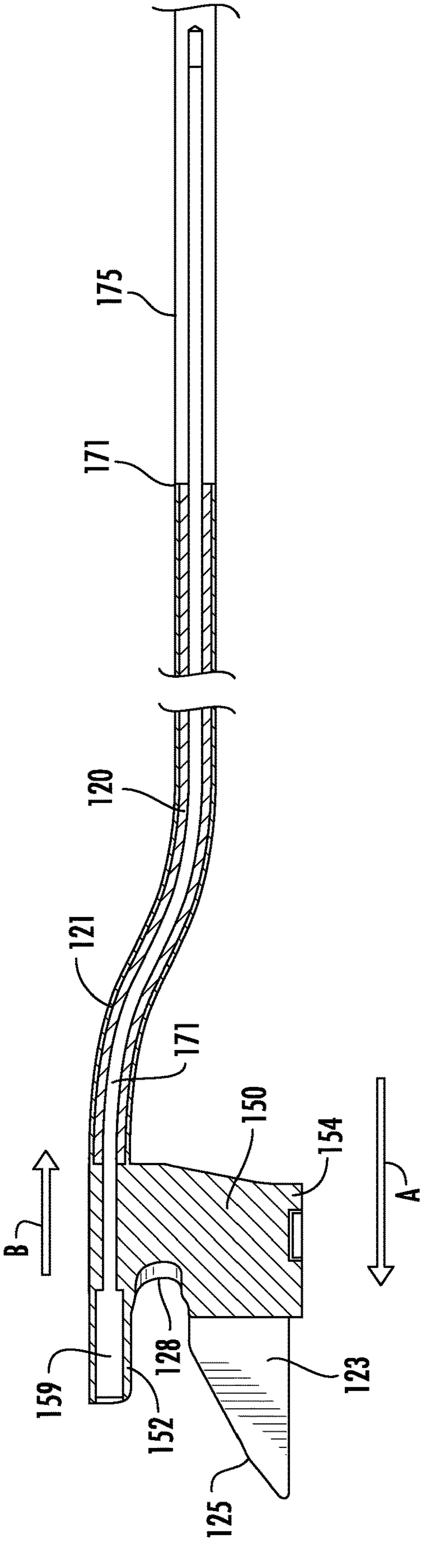
FIG. 26B is a cross-sectional side view of the actuation mechanism for a drive member in accordance with the surgical instrument of FIG. 1.

Referring now to FIGS. 26A and 26B, an actuation assembly includes a drive cable 171, a coil 120, a sheath 121 surrounding coil 120, and a drive rod 175. Drive cable 171 includes an enlarged distal end 173. Upper shoe 152 of drive member 150 includes a bore 158 into which drive cable 171 is routed. When assembling illustrative surgical instrument 100, coil 120 and a protective sheath 121 are slipped over the free end of drive cable 171. The free end of drive cable 171 is attached to a drive rod 175 securing coil 120 and the protective sheath 121 between drive member 150 and drive rod 175 as seen in FIG. 19B. Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL™, poly para-phenyleneterphtalamide materials such as KEVLAR™ commercially available from DuPont. Other suitable materials may be envisioned by those of skill in the art.

Enlarged distal end 173 of drive cable 171 resides within an enlarged distal portion 159 of bore 158 in upper shoe 152 of body 150, such that the proximal face 157 of enlarged distal end 173 may apply a retraction force on upper shoe 152 when the drive cable 171 is pulled proximally, i.e., in the direction of arrow "B" in FIG. 26B. Drive rod 175 is operationally connected to an actuator (e.g., movable handle 102*b*), which allows distal translation and proximal retraction of actuation assembly 190. Those skilled in the art will recognize that in a manually actuated instrument, the actuator may be a movable handle, such as moveable handle 102*b* shown in FIG. 1; in a powered instrument the actuator may be a button (not shown) that causes a motor to act on the drive rod; and in a robotic system, the actuator may be a control device such as the control devices described below in connection with FIG. 28. Any suitable backend actuation mechanism for driving the components of the surgical stapling instrument may be used. For additional details relating to exemplary actuation mechanisms using push/pull drive cables see, e.g., commonly owned International Application WO 2018/049217, the disclosure of which is hereby incorporated by reference in its entirety.

During actuation of illustrative surgical instrument 100, drive rod 175 applies force to coil 120, thereby causing coil 120 to apply force to upper shoe 152 of drive member 150, translating it distally (i.e., in the direction of arrow "A" in FIG. 26B) initially closing jaws 111,112 and then ejecting staples 124 from cartridge 122 to staple tissue. After stapling is complete, drive rod 175 applies a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. In certain embodiments, the surgical instrument may be designed such that the drive member 150 is not retracted in the proximal direction after the staples have been fired. One of ordinary skill in the art will appreciate that drive member 150, drive cable 171, and drive rod 175 all move in unison and remain in the same relative position to each other.

In the preferred embodiment, drive cable 171 advances drive member 150 through fixed jaw 111 (instead of through the staple cartridge jaw as in conventional surgical stapling instruments). Eliminating the internal channel for the actuation mechanism from the staple cartridge provides more space in the cartridge for the staples and for the reinforcing wall discussed above. In alternative embodiments, coil 120 of actuation assembly 190 may be coupled with lower shoe 154 instead of upper shoe 152. In these embodiments, coil 120 applies force to lower shoe 154 to advance drive member 150 distally through a channel (not shown) in the lower jaw 112. In these embodiments, coil 120 will advance at least through a portion of lower jaw 112 and staple cartridge 122.

Figure 27A:
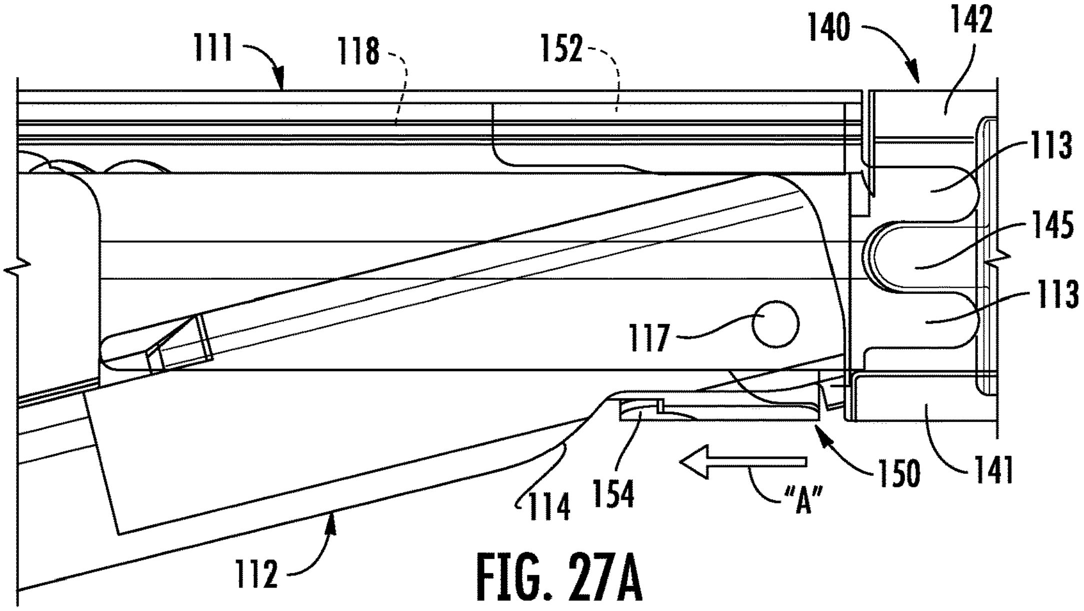
FIG. 27A shows a movable lower jaw of an illustrative surgical instrument in an open configuration.
Figure 27B:
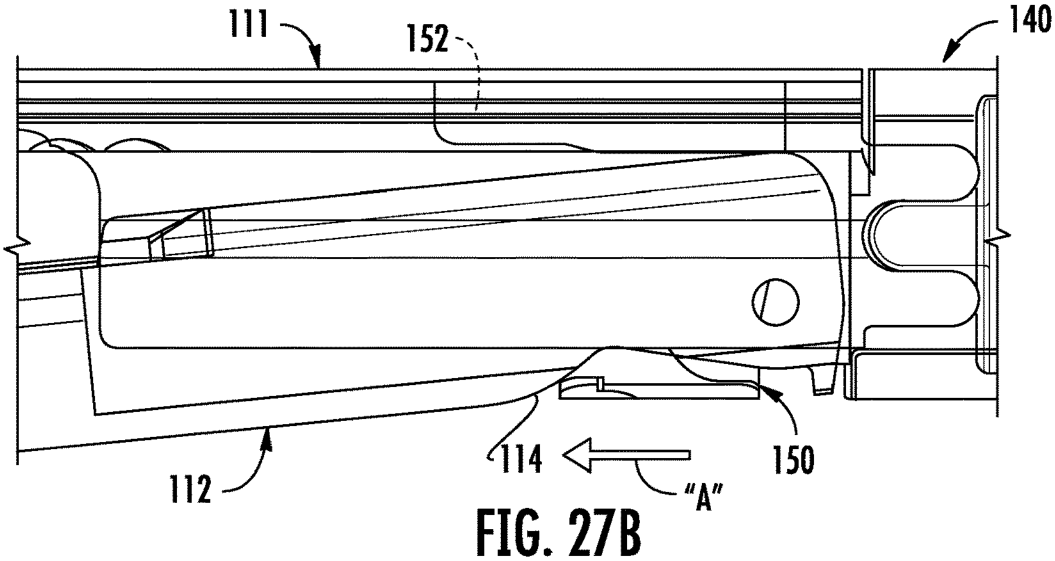
FIG. 27B shows a movable lower jaw of an illustrative surgical instrument pivoting towards a closed position.
Figure 27C:
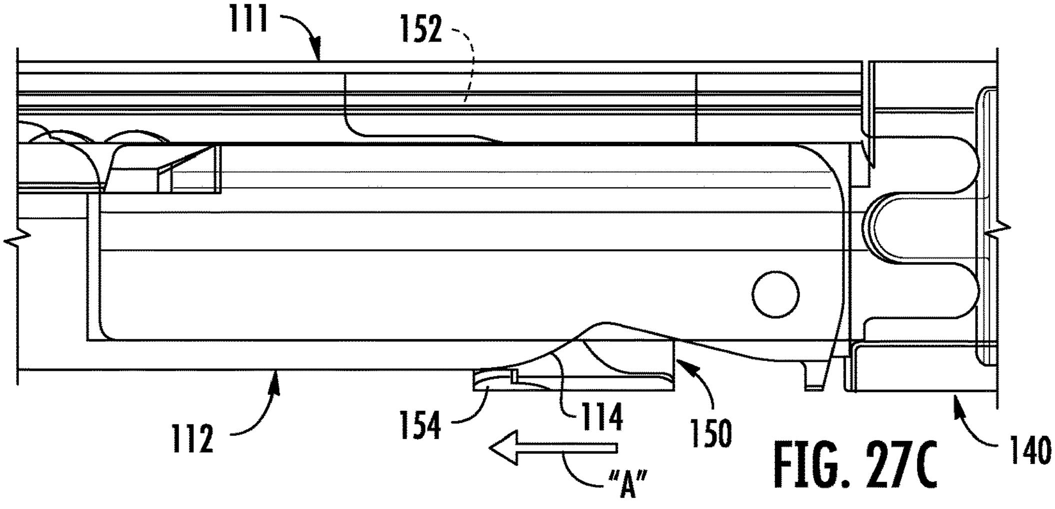
FIG. 27C shows a movable lower jaw of an illustrative surgical instrument in a closed position.

FIGS. 27A-C depict fixed jaw 111 and movable jaw 112 of illustrative surgical instrument 100 sequentially moving from an open configuration to a closed configuration. As shown in FIG. 27A, in the open configuration, drive member 150 is positioned proximally of cam surface 114 formed on movable jaw 112. As drive member 150 translates in the distal direction "A" movable jaw 112 will rotate towards the closed position around pivot 117.

In FIG. 27B, drive member 150 has come into contact with cam surface 114 of movable jaw 112. As lower portion 154 of drive member 150 rides underneath cam surface 114, drive member 150 pushes movable jaw 112, causing it to pivot towards the closed position.

FIG. 27C illustrates jaws 111, 112 in the closed position. Drive member 150 has translated distally past cam surface 114. In this position, tissue is clamped, and further advancement of the drive member will sever and staple tissue.

In embodiments, surgical instruments may alternatively include switches configured to be sheared along an axis, or switches having vertical cutouts designed to be engaged by an inclined distal portion of a drive member for purposes of engaging a lockout assembly, providing for reload recognition, or both, as described in International Patent Application Nos. PCT/US2019/66513 and PCT/US2019/66530, both filed on Dec. 16, 2019, the entire disclosures of which are incorporated herein by reference.

Figure 28:
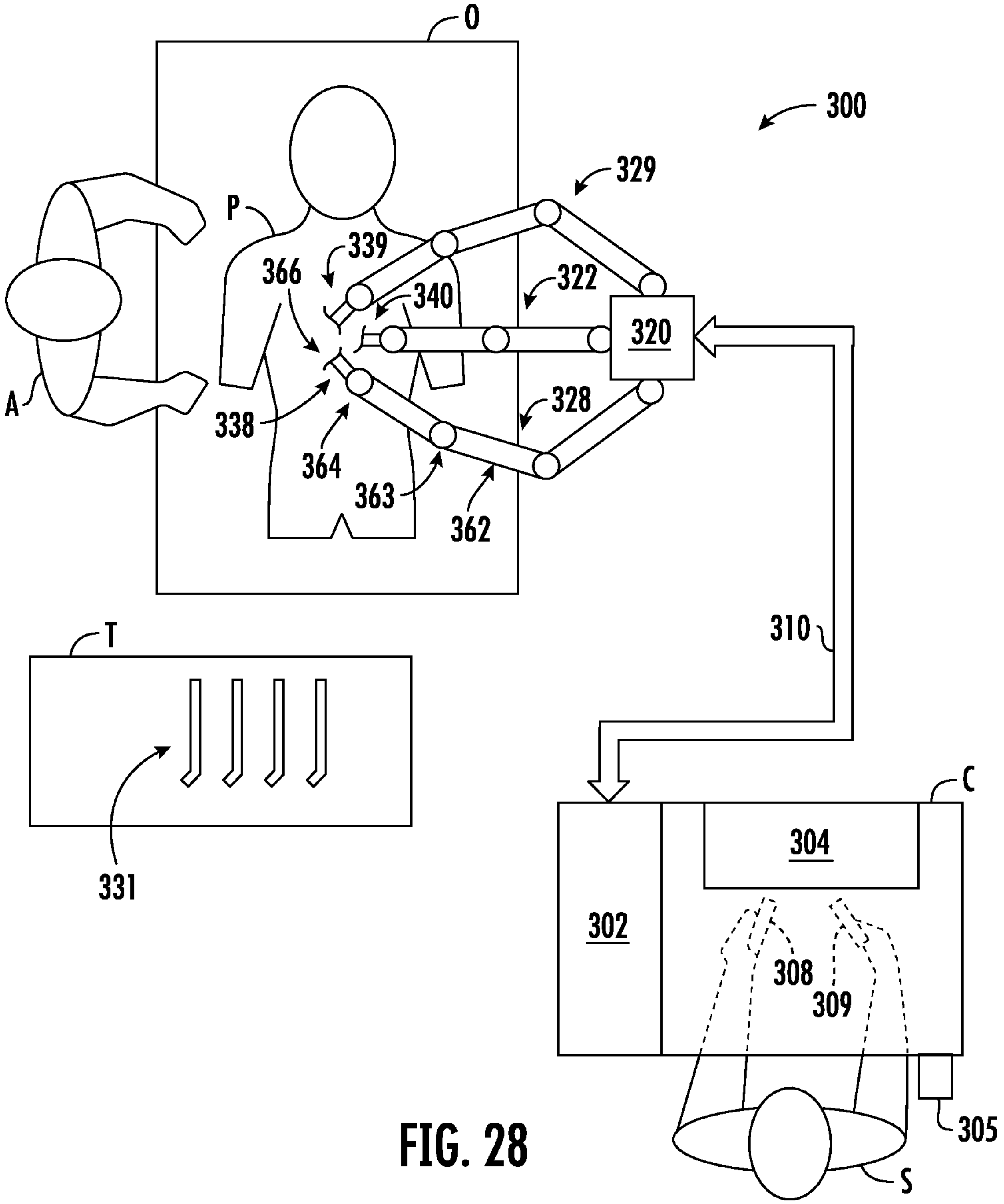
FIG. 28 illustrates a top view of an operating room employing a robotic surgical system.

FIG. 28 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware.

For additional details on robotic surgical systems, see, e.g., commonly owned U.S. Pat. No. 6,493,608, U.S. Pat. No. 6,671, and International Application WO 2017/132611. Each of these disclosures is herein incorporated in its entirety by this reference.

Figure 29:
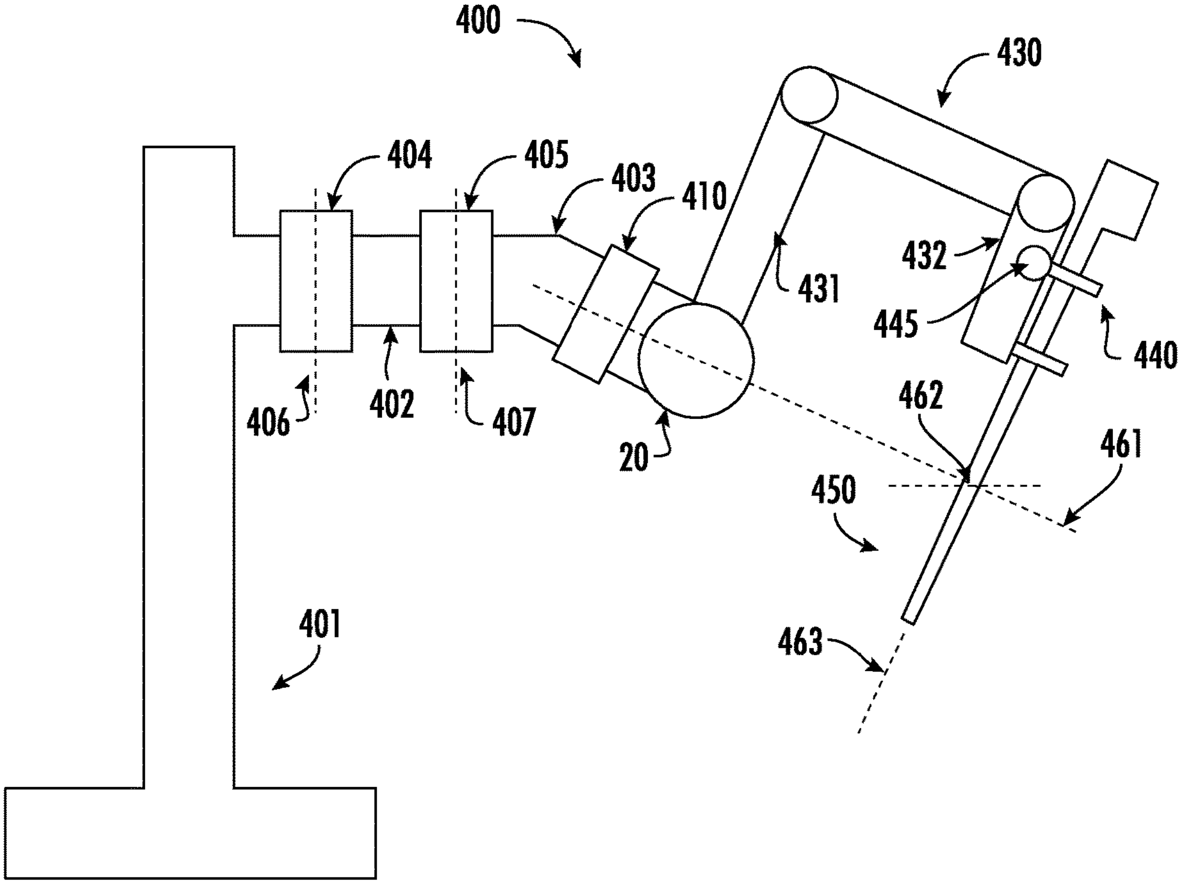
FIG. 29 illustrates a simplified side view of a robotic arm assembly.

FIG. 29 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403 which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407.

Although only two links and two setup joints are shown in this example, more or less of each may be used as appropriate in this and other robotic arm assemblies described herein. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator.

While several embodiments have been shown in the drawings, it is not intended that the disclosure be limited thereto, as it is intended that the disclosure be as broad in scope as the art will allow and that the specification be read likewise. For example, the devices disclosed herein are not limited to the mechanisms described herein for identifying and/or deactivating stapler cartridges. Other suitable devices or mechanisms are described in co-pending and co-owned International Patent Application No. PCT/US19/66513, filed Dec. 16, 2019 and entitled "SURGICAL INSTRUMENTS WITH SWITCHES FOR DEACTIVATING AND/OR IDENTIFYING STAPLER CARTRIDGES", the complete disclosure of which is herein incorporated by reference in its entirety for all purposes. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical instrument comprising:

an end effector having first and second jaws;

a drive member configured to translate distally through the end effector;

a stapler cartridge comprising a housing defining a longitudinal axis and having at least one row of staple pockets for receiving staples therein and a channel for receiving the drive member;

a switch defining a proximal portion and a distal portion and having a contact surface on the proximal portion at least partially disposed within the channel such that the drive member engages the contact surface and moves the switch as the drive member translates through the channel;

a locking member movable from a disabled position permitting translation of the drive member through the channel, to a locking position inhibiting translation of the drive member through the channel, wherein the switch is movable in a lateral direction relative to the longitudinal axis, from a first position wherein the switch maintains the locking member in the disabled position to a second position wherein the switch disengages the locking member; and wherein the contact surface extends transversely into the channel at an angle of less than about 45 degrees with the longitudinal axis.

2. The surgical instrument of claim 1, wherein the angle is less than about 30 degrees.

3. The surgical instrument of claim 1, wherein the contact surface extends from a proximal end of the switch to a position at least about halfway to a midpoint between the proximal and distal ends.

4. The surgical instrument of claim 1, wherein the contact surface extends to at least the midpoint between the proximal and distal ends of the switch.

5. The surgical instrument of claim 1, wherein the contact surface comprises a first surface extending transversely into the channel and at least a second surface distal to the first surface and extending transversely into the channel from the first surface in a distal direction, wherein the second surface defines a smaller angle with the longitudinal axis than the first surface.

6. The surgical instrument of claim 5, wherein the drive member contacts the first and second surfaces as the drive member moves distally through the channel.

7. The surgical instrument of claim 1, wherein the switch is movable in a lateral direction as the drive member engages the contact surface.

8. The surgical instrument of claim 1, wherein the switch is positioned within a slot formed on a proximal portion of the staple cartridge, wherein the slot formed on the proximal portion of the cartridge includes one or more detents formed therein, the detents being configured to provide mechanical resistance when the drive member engages the switch.

9. The surgical instrument of claim 1, wherein the switch is configured to provide a detectable resistance upon engagement of the drive member with the contact surface.

10. The surgical instrument of claim 9, wherein the cartridge is operatively coupled to a control unit, the control unit configured to process the detectable resistance to identify the stapler cartridge, wherein the control unit includes a control device of a robotic surgical system.

11. A surgical instrument comprising:

an end effector having first and second jaws;

a drive member configured to translate distally through the end effector;

a stapler cartridge disposed within the second jaw and comprising a housing defining a longitudinal axis and having a tissue contacting surface facing the first jaw with at least one row of staple pockets for receiving staples therein and a channel for receiving the drive member, the housing further comprising a proximal portion with an upper surface disposed more proximate to the first jaw than the tissue contacting surface of the housing, wherein the upper surface is disposed laterally from the channel relative to the longitudinal axis;

a switch having a contact surface at least partially disposed within the channel such that the drive member contacts the contact surface as the drive member translates through the channel; and two or more protrusions extending towards the first jaw from the upper surface of the proximal portion of the housing.

12. The surgical instrument of claim 11, wherein the protrusions are deformable.

13. The surgical instrument of claim 11, wherein the the first jaw is an upper jaw and the second jaw is a lower jaw movable between open and closed positions, the second lower jaw having a cavity for receiving the cartridge, wherein the protrusions extend from the upper surface of the proximal portion of the cartridge to a lower surface of the first jaw when the first and second jaws are in the closed positions.

14. The surgical instrument of claim 11, wherein the protrusions taper inwardly from a first end portion to a second end.

15. A surgical instrument comprising:

an end effector having first and second jaws;

a drive member configured to translate distally through the end effector;

a stapler cartridge comprising a housing defining a longitudinal axis and having at least one row of staple pockets for receiving staples therein and a channel for receiving the drive member;

a switch defining a proximal portion and a distal portion and having a contact surface on the proximal portion at least partially disposed within the channel such that the drive member engages the contact surface and moves the switch as the drive member translates through the channel; and wherein the contact surface extends transversely into the channel at an angle of less than about 45 degrees with the longitudinal axis and wherein the contact surface comprises a first surface extending transversely into the channel and at least a second surface distal to the first surface and extending transversely into the channel from the first surface in a distal direction, wherein the second surface defines a smaller angle with the longitudinal axis than the first surface.

16. The surgical instrument of claim 15, wherein the angle is less than about 30 degrees.

17. The surgical instrument of claim 16, wherein the contact surface extends from a proximal end of the switch to a position at least about halfway to a midpoint between the proximal and distal ends.

18. The surgical instrument of claim 16, wherein the contact surface extends to at least the midpoint between the proximal and distal ends of the switch.

19. The surgical instrument of claim 16, wherein the switch is positioned within a slot formed on a proximal portion of the staple cartridge, wherein the slot formed on the proximal portion of the cartridge includes one or more detents formed therein, the detents being configured to provide mechanical resistance when the drive member engages the switch.

20. The surgical instrument of claim 16, wherein the switch is configured to provide a detectable resistance upon engagement of the drive member with the contact surface.

* * * * *